(12) United States Patent
Holoboski et al.

(10) Patent No.: US 8,487,091 B2
(45) Date of Patent: *Jul. 16, 2013

(54) SUBSTITUTED CYCLOPENTANES HAVING PROSTAGLANDIN ACTIVITY

(75) Inventors: Mark Holoboski, Irvine, CA (US);
Robert M. Burk, Laguna Beach, CA (US); Mari Posner, Laguna Niguel, CA (US); Yariv Donde, Dana Point, CA (US); David W. Old, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 94 days.

This patent is subject to a terminal disclaimer.

(21) Appl. No.: 12/392,571

(22) Filed: Feb. 25, 2009

(65) Prior Publication Data

US 2009/0227573 A1 Sep. 10, 2009

Related U.S. Application Data

(60) Provisional application No. 60/033,705, filed on Mar. 4, 2008, provisional application No. 61/037,245, filed on Mar. 17, 2008.

(51) Int. Cl.
*C07D 345/00* (2006.01)
*C07D 517/00* (2006.01)

(52) U.S. Cl.
USPC ............ 540/1; 514/231.5; 514/448; 544/146; 549/71

(58) Field of Classification Search
USPC ............................... 514/448; 544/146; 549/71
See application file for complete search history.

(56) References Cited

U.S. PATENT DOCUMENTS 7,091,231 B2  8/2006 Donde

FOREIGN PATENT DOCUMENTS

WO  WO 2007149829 A2 * 12/2007

OTHER PUBLICATIONS

Kosuke, Tani, et al.: Development of Highly Selective EP2-Receptor Agonist. Part 1: Identification of 16-Hydroxy-17, 17-Trimethylene PGE2 Derivatives. Bioorg. Med. Chem.2002, 10, 1093-1106.
Silverman, Richard: Organic Chemistry of Drug Design and Drug Action, 2d Ed., Elsevier Academic Press: Amsterdam, 2004, pp. 496-557.

* cited by examiner

*Primary Examiner* — Brandon Fetterolf
*Assistant Examiner* — Jean Cornet
(74) *Attorney, Agent, or Firm* — Allergan, Inc.

(57) ABSTRACT

Disclosed herein are compounds represented by the formula:

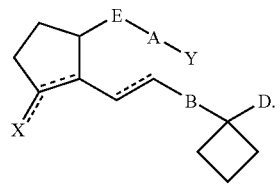

Therapeutic methods, compositions, and medicaments related thereto are also disclosed.

8 Claims, No Drawings

SUBSTITUTED CYCLOPENTANES HAVING PROSTAGLANDIN ACTIVITY

RELATED APPLICATION

This application claims the benefit of U.S. Provisional Application Ser. No. 61/033,705, filed Mar. 4, 2008 and 61/037,245, filed Mar. 17, 2008, the disclosures of which are hereby incorporated in their entirety herein by reference.

DESCRIPTION OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract. Glaucoma occurs in about 2% of all persons over the age of 40 and may be asymptotic for years before progressing to rapid loss of vision.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupilary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe, and may plug the drainage channel with exudates. Other common causes are intraocular tumors, enlarged cataracts, central retinal vein occlusion, trauma to the eye, operative procedures and intraocular hemorrhage.

In cases where surgery is not indicated, prostaglandins and prostamides have recently become the first line treatments of glaucoma. Certain eicosanoids and their derivatives are currently commercially available for use in glaucoma management. Eicosanoids and derivatives include numerous biologically important compounds such as prostaglandins and their derivatives. Prostaglandins can be described as derivatives of prostanoic acid which have the following structural formula:

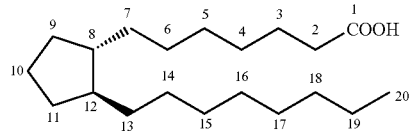

Various types of prostaglandins are known, depending on the structure and substituents carried on the alicyclic ring of the prostanoic acid skeleton. Further classification is based on the number of unsaturated bonds in the side chain indicated by numerical subscripts after the generic type of prostaglandin [e.g. prostaglandin $E_1$ ($PGE_1$), prostaglandin $E_2$ ($PGE_2$)], and on the configuration of the substituents on the alicyclic ring indicated by α or β [e.g. prostaglandin $F_{2\alpha}$ ($PGF_{2\beta}$)].

Disclosed herein are compounds represented by the formula:

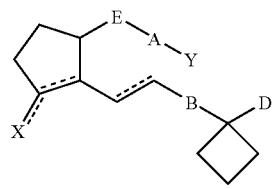

wherein a dashed line represents the presence or absence of a bond;
Y has from 0 to 14 carbon atoms and is: an organic acid functional group, or an amide or ester thereof; hydroxymethyl or an ether thereof; or a tetrazolyl functional group;
A is aryl or heteroaryl having a formula $C_{0-8}H_{0-19}N_{0-2}O_{0-2}S_{0-2}F_{0-3}Cl_{0-2}Br_{0-2}I_{0-2}$;
E is $-(CH_2)_3-$, cis $-CH_2-CH=CH-$, $-O-(CH_2)_2$, $-CH_2OCH_2-$, $-(CH_2)_2O-$, $-S-(CH_2)_2$, $-CH_2SCH_2$, or $-(CH_2)_2S-$;
X is H, F, Cl, Br, I, O, or CN;
B is hydroxyalkyl having from 1 to 5 carbon atoms;
D is alkyl, aryl, heteroaryl, arylalkyl, or heteroarylalkyl having a formula $C_{0-8}H_{0-19}N_{0-2}O_{0-2}S_{0-2}F_{0-3}Cl_{0-2}Br_{0-2}I_{0-2}$.

These compounds are useful for reducing intraocular pressure. Reduction of intraocular pressure has been shown to delay or prevent the onset of primary open angle glaucoma, and to delay or prevent further vision loss in patients with primary open angle glaucoma. Thus, these compounds are also useful for treating glaucoma. These compounds are also useful for growing hair, including one or more of: increasing the number of individual hairs, increasing the length of individual hairs, and increasing the diameter or thickness of individual hairs. These compounds are also useful for improving the appearance of hair, including increasing its gloss, shine, or other properties related to the reflection or dispersion of light, as well as changing the color of hair, including changing hair from grey or white to the color the hair was before it turned grey or white, such as red, brown, or black.

One embodiment is a method of reducing intraocular pressure comprising administering a compound disclosed herein to mammal in need thereof.

Another embodiment is use of a compound disclosed herein in the manufacture of a medicament for the reduction of intraocular pressure in a mammal.

Another embodiment is a method of treating glaucoma comprising administering a compound disclosed herein to a mammal in need thereof.

Another embodiment is an ophthalmically acceptable liquid comprising a compound disclosed herein and an ophthalmically acceptable vehicle.

Another embodiment is a method of growing hair or improving the appearance of hair comprising administering a compound disclosed herein to a mammal in need thereof.

Another embodiment is use of a compound disclosed herein in the manufacture of medicament for growing hair or improving the appearance of hair of a mammal.

Different types of suitable dosage forms and medicaments are well known in the art, and can be readily adapted for delivery of the compounds disclosed herein. For example, the compound could be dissolved or suspended in an aqueous solution or emulsion that is buffered to an appropriate pH, and administered topically to an eye of a mammal (see U.S. Pat. No. 7,091,231).

For the purposes of this disclosure, "treat," "treating," or "treatment" refer to the use of a compound, composition, therapeutically active agent, or drug in the diagnosis, cure, mitigation, treatment, or prevention of disease or other undesirable condition.

Unless otherwise indicated, reference to a compound should be construed broadly to include compounds, pharmaceutically acceptable salts, prodrugs, tautomers, alternate solid forms, non-covalent complexes, and combinations thereof, of a chemical entity of a depicted structure or chemical name.

A pharmaceutically acceptable salt is any salt of the parent compound that is suitable for administration to an animal or human. A pharmaceutically acceptable salt also refers to any salt which may form in vivo as a result of administration of an acid, another salt, or a prodrug which is converted into an acid or salt. A salt comprises one or more ionic forms of the compound, such as a conjugate acid or base, associated with one or more corresponding counter-ions. Salts can form from or incorporate one or more deprotonated acidic groups (e.g. carboxylic acids), one or more protonated basic groups (e.g. amines), or both (e.g. zwitterions).

A prodrug is a compound which is converted to a therapeutically active compound after administration. For example, conversion may occur by hydrolysis of an ester group or some other biologically labile group. Prodrug preparation is well known in the art. For example, "Prodrugs and Drug Delivery Systems," which is a chapter in Richard B. Silverman, *Organic Chemistry of Drug Design and Drug Action,* 2d Ed., Elsevier Academic Press. Amsterdam, 2004, pp. 496-557, provides further detail on the subject. In particular, alkyl esters having such as methyl, ethyl, isopropyl, and the like are contemplated. Also contemplated are prodrugs containing a polar group such as hydroxyl or morpholine. Examples of such prodrugs include compounds containing the moieties —CO$_2$(CH$_2$)$_2$OH,

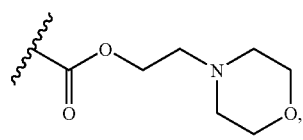

and the like.

Tautomers are isomers that are in rapid equilibrium with one another. For example, tautomers may be related by transfer of a proton, hydrogen atom, or hydride ion.

Unless stereochemistry is explicitly and unambiguously depicted, a structure is intended to include every possible stereoisomer, both pure or in any possible mixture.

Alternate solid forms are different solid forms than those that may result from practicing the procedures described herein. For example, alternate solid forms may be polymorphs, different kinds of amorphous solid forms, glasses, and the like.

Non-covalent complexes are complexes that may form between the compound and one or more additional chemical species that do not involve a covalent bonding interaction between the compound and the additional chemical species. They may or may not have a specific ratio between the compound and the additional chemical species. Examples might include solvates, hydrates, charge transfer complexes, and the lie.

A dashed line indicates the presence or absence of a bond. Therefore, compounds according to the structures below are possible.

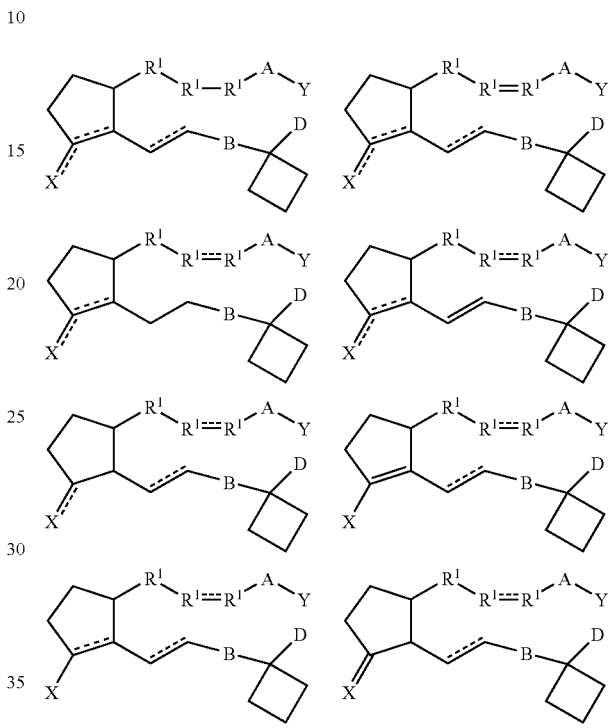

Y has from 0 to 14 carbon atoms and is: an organic acid functional group, or an amide or ester thereof; hydroxymethyl or an ether thereof; or a tetrazolyl functional group. For the purposes of this disclosure, Y is limited to from 0 to 14 carbon atoms, from 0 to 5 oxygen atoms, from 0 to 2 nitrogen atoms, from 0 to 2 sulfur atoms, from 0 to 1 phosphorous, and any necessary hydrogen atoms.

An organic acid functional group is an acidic functional group on an organic molecule. For example, organic acid functional groups may comprise an oxide of carbon, sulfur, or phosphorous. Thus, while not intending to limit the scope of the invention in any way, in certain compounds Y is a carboxylic acid, sulfonic acid, or phosphonic acid functional group.

Esters of organic acid functional groups have an oxygen atom directly attached to the acidic core atom, where the oxygen atom is not part of an —OH moiety. Amides of organic acid functional groups have a nitrogen directly attached to the acidic core atom. The acidic core atom is the atom that is bonded to —OH or —SH in the organic acid functional group. For example, the carbonyl carbon is the acidic core atom of a carboxylic acid, the sulfonyl sulfur is the acidic core atom of a sulfonic acid, and the phosphonyl phosphorous is the acidic core atom of a phosphonic acid. To further exemplify this principle, esters of amides of carboxylic acids, sulfonic acid, and phosphonic acid functional groups are depicted below.

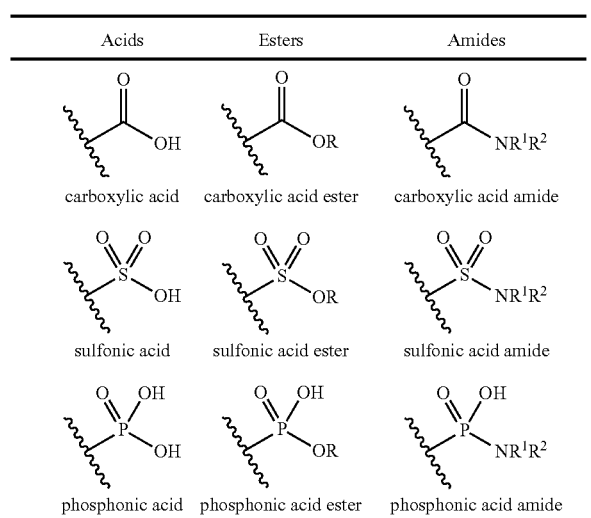

R, $R^1$, $R^2$, and $R^3$ are hydrocarbyl subject to the constraint that Y may not have more than 14 carbon atoms.

An amide may also have an —$SO_2$— moiety. For example the amide —$CONHSO_2R^3$, wherein $R^3$ is a hydrocarbyl of from 1 to 14 carbon atoms, is contemplated.

Hydrocarbyl is a moiety consisting of carbon and hydrogen, including, but not limited to:
a. alkyl, which is hydrocarbyl that contains no double or triple bonds, such as:
   linear alkyl, e.g. methyl, ethyl, n-propyl, n-butyl, n-pentyl, n-hexyl, etc.,
   branched alkyl, e.g. iso-propyl, t-butyl and other branched butyl isomers, branched pentyl isomers, etc.,
   cycloalkyl, e.g. cyclopropyl, cyclobutyl, cyclopentyl, cyclohexyl, etc.,
   combinations of linear, branched, and/or cycloalkyl;
b. alkenyl, which is hydrocarbyl having 1 or more double bonds, including linear, branched, or cycloalkenyl;
c. alkynyl, which is hydrocarbyl having 1 or more triple bonds, including linear, branched, or cycloalkynyl;
d. unsubstituted or hydrocarbyl substituted phenyl; and
e. combinations of alkyl, alkenyl, akynyl, and/or phenyl.

$C_{1-6}$ hydrocarbyl is hydrocarbyl having 1, 2, 3, 4, 5, or 6 carbon atoms.

$C_{1-6}$ alkyl is alkyl having 1, 2, 3, 4, 5, or 6, carbon atoms such as methyl, ethyl, propyl isomers, butyl isomers, pentyl isomer, and hexyl isomers, etc.

An unsubstituted tetrazolyl functional group has two tautomeric forms, which can rapidly interconvert in aqueous or biological media, and are thus equivalent to one another. These tautomers are shown below.

Additionally, if $R^2$ is $C_1$-$C_6$ alkyl, phenyl, or biphenyl, other isomeric forms of the tetrazolyl functional group such as the one shown below are also possible, unsubstituted and hydrocarbyl substituted tetrazolyl up to $C_{14}$ are considered to be within the scope of the term "tetrazolyl."

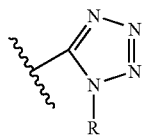

In one embodiment, Y is —$CO_2R^4$, —$CONR^5R^6$, —$CON(CH_2CH_2OH)_2$, —$CONH(CH_2CH_2OH)$, —$CH_2OH$, —$P(O)(OH)_2$, —$CONHSO_2R^4$, —$SO_2NR^5R^6$, wherein $R^4$, $R^5$ and $R^6$ are independently H, $C_1$-$C_6$ alkyl, $C_{1-6}$ hydroxyalkyl, unsubstituted phenyl, or unsubstituted biphenyl, provided that Y has no more than 14 carbon atoms.

A is aryl or heteroaryl having a formula $C_{0-8}H_{0-19}N_{0-2}O_{0-2}S_{0-2}F_{0-3}Cl_{0-2}Br_{0-2}I_{0-2}$.

As used anywhere herein, the phrase "having a formula" followed by an empirical formula such as $C_{0-8}H_{0-19}N_{0-2}O_{0-2}S_{0-2}F_{0-3}Cl_{0-2}Br_{0-2}I_{0-2}$ means that the moiety described by that follows the following rules:
  All carbon atoms in the moiety described by that formula have 4 covalent bonds.
  Every hydrogen, fluorine, chlorine, bromine, and iodine atom of a compound disclosed herein has 1 covalent bond.
  Every oxygen atom of a compound disclosed herein has 2 covalent bonds unless the oxygen atom is anionic, in which case the oxygen atom has 1 covalent bond.
  Every sulfur atom of a compound disclosed herein has 2 covalent bonds, except in the case of sulfonyl (—$SO_2$—) or sulfoxide (—SO—) functional groups.
  Every nitrogen atom of a compound disclosed herein has 3 covalent bonds unless the nitrogen atom is cationic, in which case it has 4 covalent bonds, such as in a quaternary ammonium salt (e.g. $N(CH_3)_4^+$) or a nitro (—$NO_2$) functional group.
  No more than 2 heteroatoms (heteroatoms are anything other than C and H) are consecutively bonded to one another. For example, —O—O—O—, —N—O—O—, —S—S—S—, and —O—S—Cl are excluded.
  A double bond counts as 2 covalent bonds and a triple bond counts as 3 covalent bonds.

$C_{0-8}H_{0-19}N_{0-2}O_{0-2}S_{0-2}F_{0-3}Cl_{0-2}Br_{0-2}I_{0-2}$ means that the moiety contains from 0-8 carbon atoms, from 0-19 hydrogen atoms, from 0-2 nitrogen atoms, from 0-2 oxygen atoms, from 0-2 sulfur atoms, from 0-3 fluorine atoms, from 0-2 chlorine atoms, from 0-2 bromine atoms, and from 0-2 iodine atoms.

In one embodiment, if Cl, Br, or I are present, they are present only as a substituent on an aromatic ring. In other words, the substituent is Cl, Br, or I.

In another embodiment, if F is present, it is present only as a substituent on an aromatic ring or as part of $CF_3$.

Aryl is a substituted or unsubstituted aromatic ring or ring system such as phenyl. Heteroaryl is a substituted or unsubstited aromatic ring or ring system containing one or more N, O, and/or S atoms in the ring. Examples of heteroaryl include thienyl, furyl, pyridinyl, oxazolyl, thiazolyl, imidazolyl, etc.

Both aryl and heteroaryl can be substituted, meaning that they may have one or more substituents, up to as many as the ring or ring system will bear.

In one embodiment, aryl or heteroaryl has from 0 to 4 substituents.

In another embodiment, aryl or heteroaryl has from 0 to 3 substituents.

In another embodiment, aryl or heteroaryl has from 0 to 2 substituents.

In another embodiment, aryl or heteroaryl has from 0 to 1 substituent.

In another embodiment, aryl or heteroaryl is unsubstituted.

Some examples of substituents on aryl and heteroaryl include:
- alkyl, such as methyl, ethyl, propyl, isopropyl, butyl isomers, etc.;
- hydroxyalkyl, meaning -alkyl-OH, such as hydroxymethyl, —CH$_2$CH$_2$OH, —CHCHOHCH$_3$, etc.;
- halogens, such as fluoro, chloro, bromo, and iodo;
- amines, such as —NH$_2$, methylamine, dimethylamine, etc.;
- ethers such as —O-alkyl;
- thioethers such as —S-alkyl;
- acyl, i.e.

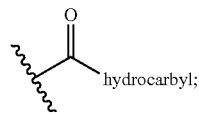

acyloxy, i.e.

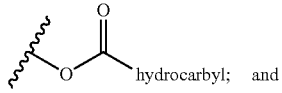

other substituents such as OH, SH, CO$_2$H, NO$_2$, CN, CF$_3$, etc.

E is —(CH$_2$)$_3$—, cis —CH$_2$—CH=CH—, —O—(CH$_2$)$_2$, —CH$_2$OCH$_2$, —(CH$_2$)$_2$O—, —S—(CH$_2$)$_2$, —CH$_2$SCH$_2$, or —(CH$_2$)$_2$S—;

In one embodiment E is —(CH$_2$)$_3$—.
In another embodiment E is cis —CH$_2$—CH=CH—.
In another embodiment E is —O—(CH$_2$)$_2$.
In another embodiment E is —CH$_2$OCH$_2$.
In another embodiment E is —(CH$_2$)$_2$O—.
In another embodiment E is —S—(CH$_2$)$_2$.
In another embodiment E is —CH$_2$SCH$_2$.
In another embodiment E is —(CH$_2$)$_2$S—.

X is H, F, Cl, Br, I, O, or CN.

Thus, compounds according to any of the structures below are possible.

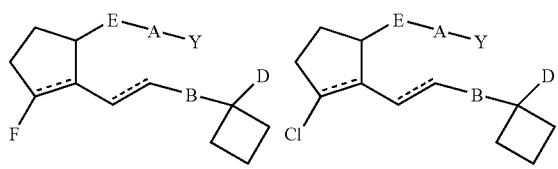

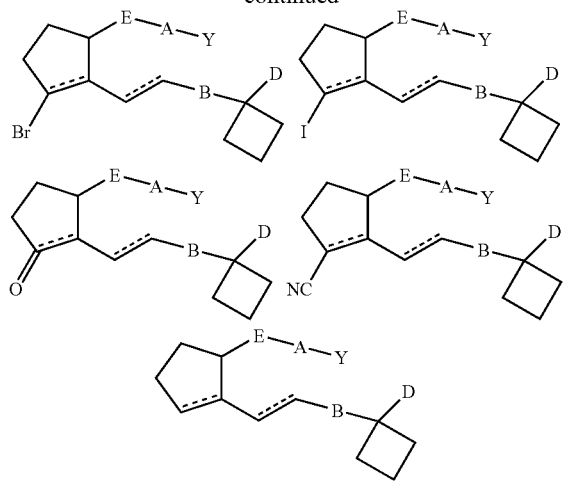

B is hydroxyalkyl having from 1 to 5 carbon atoms.
Hydroxyalkyl is described above.

In one embodiment B, is linear hydroxyalkyl having from 1 to 5 atoms. Linear hydroxyalkyl means that B is a linear alkyl chain with a hydroxyl group as a pendant substituent group, such as one of the examples shown below.

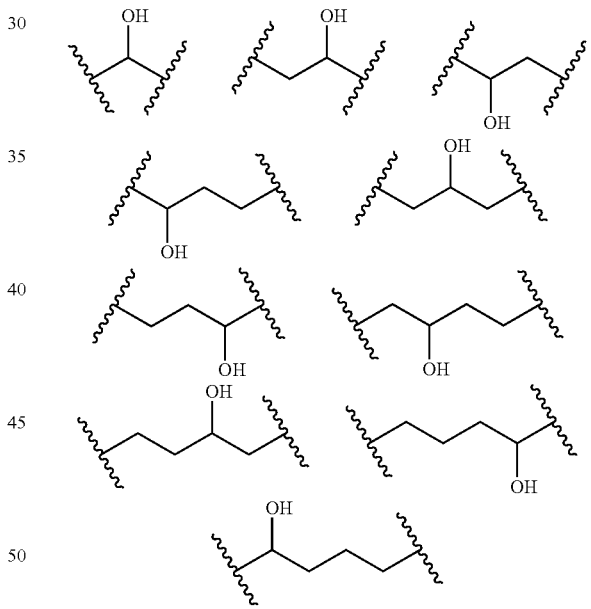

D is alkyl, aryl, heteroaryl, arylalkyl, or heteroarylalkyl having a formula C$_{0-8}$H$_{0-19}$N$_{0-2}$O$_{0-2}$S$_{0-2}$F$_{0-3}$Cl$_{0-2}$Br$_{0-2}$I$_{0-2}$.

C$_{0-8}$H$_{0-19}$N$_{0-20}$O$_{0-2}$S$_{0-2}$F$_{0-3}$Cl$_{0-2}$Br$_{0-2}$I$_{0-2}$ means that the moiety contains from 0-8 carbon atoms, from 0-19 hydrogen atoms, from 0-2 nitrogen atoms, from 0-2 oxygen atoms, from 0-2 sulfur atoms, from 0-3 fluorine atoms, from 0-2 chlorine atoms, from 0-2 bromine atoms, and from 0-2 iodine atoms.

Alkyl is described above.
Aryl is described above.
Heteroaryl is described above.
Arylalkyl is -alkyl-aryl, where aryl is described above. For example, —CH$_2$-aryl such as —CH$_2$-phenyl, and —CH₂CH₂-aryl such as —CH₂CH₂-phenyl, are contemplated wherein aryl and phenyl are substituted or unsubstituted.

Heteroarylalkyl is -alkyl-heteraryl, where heteroaryl is described above. For example, —CH₂-aryl such as —CH₂-furyl, —CH₂-thienyl, —CH₂-pyridinyl; and —CH₂CH₂-aryl such as —CH₂CH₂-furyl, —CH₂CH₂-thienyl, —CH₂CH₂-pyridinyl, are contemplated wherein heteroaryl, furyl, thienyl, and pyridinyl are substituted or unsubstituted.

The substituents for D are the same as those described above, both in the kind of substituents and the number of substituents that may be present on the ring.

In one embodiment, D is —(CH₂)ₙ-Q, wherein n is 0, 1 or 2 and Q is substituted or unsubstituted and is one of: methyl, phenyl, furyl, thienyl, and pyridinyl.

In another embodiment, Q is methyl.

In another embodiment, Q is phenyl, furyl, thienyl or pyridinyl having from 0 to 2 substituents, said substituents being selected from F, Cl, Br, I, CF₃, CH₃, OH, and OCH₃.

Some hypothetical examples of useful compounds include those shown below.

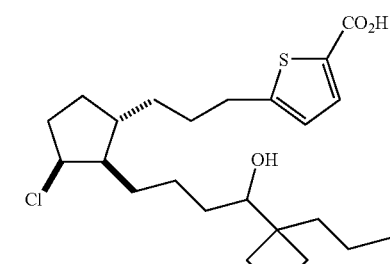

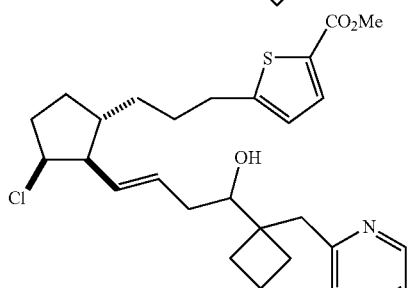

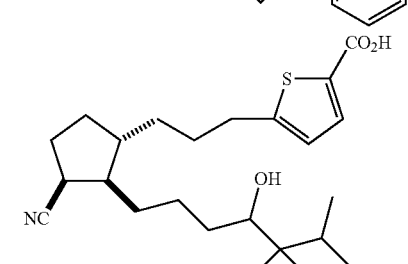

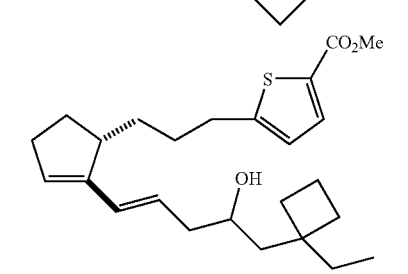

-continued

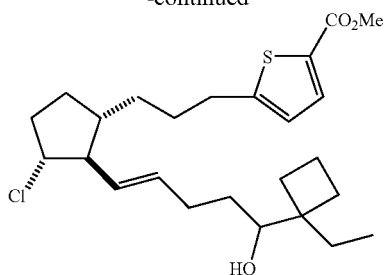

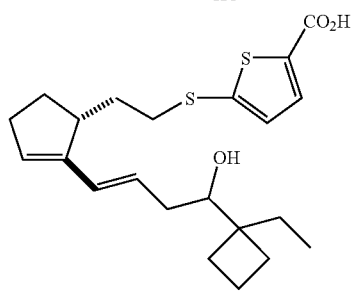

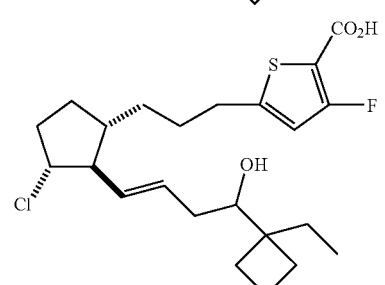

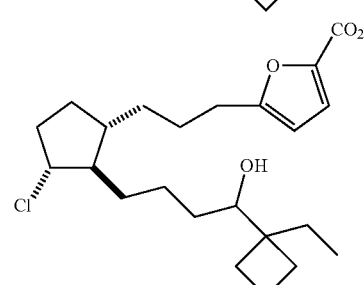

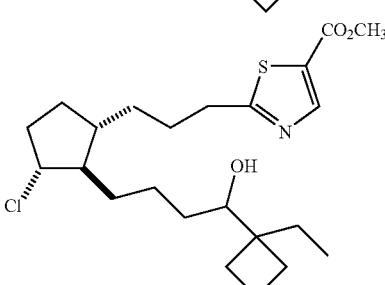

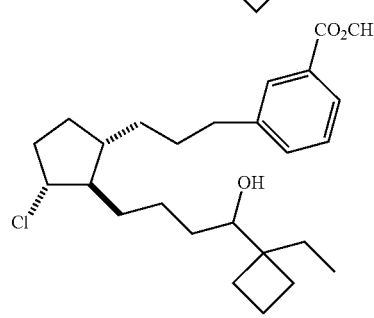

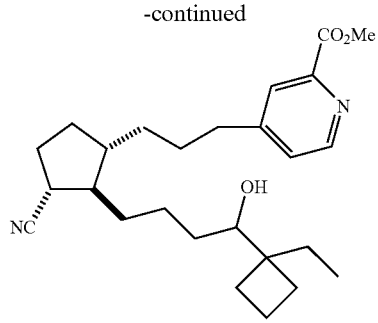
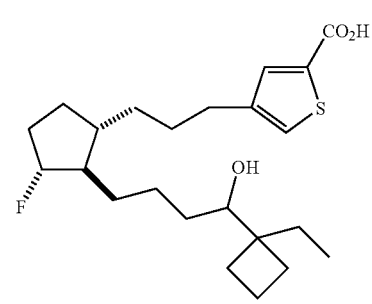
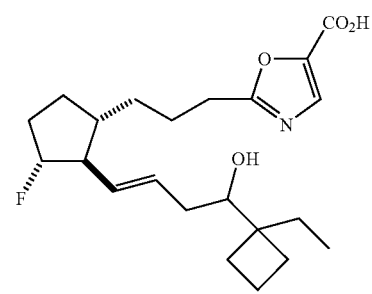
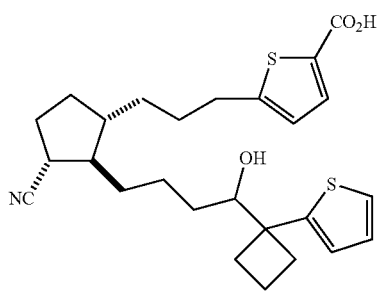
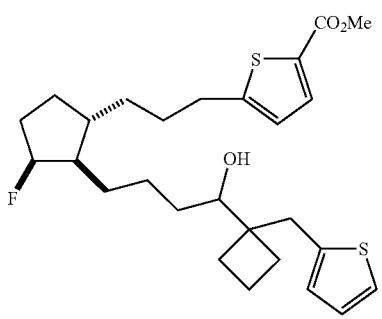
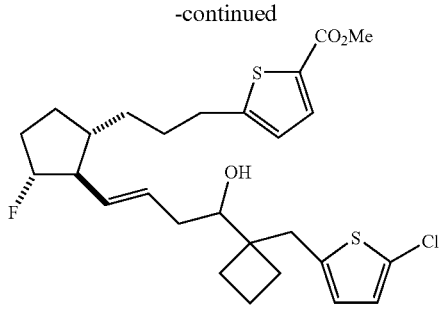
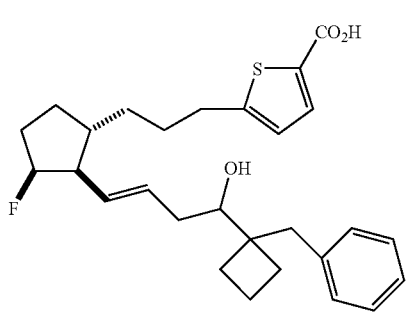
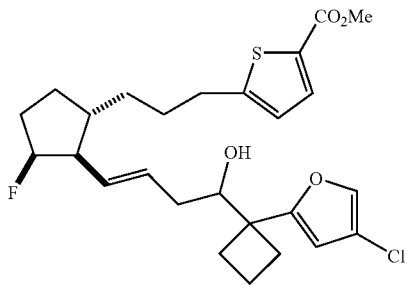
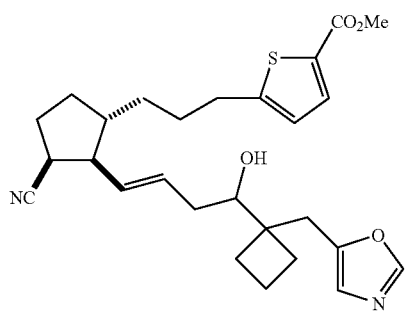
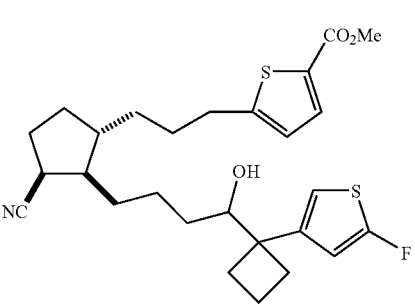

-continued

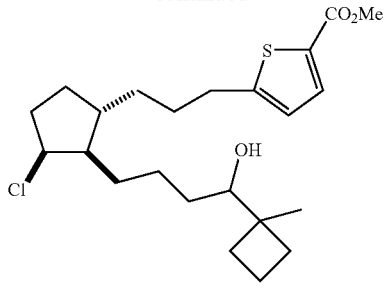

In one embodiment, Y is a carboxylic acid or an amide or ester thereof having from 0 to 14 carbon atoms.

In another embodiment, E is —(CH$_2$)$_3$—, —(CH$_2$)$_2$O—, or —(CH$_2$)$_2$S—.

In another embodiment, D is —(CH$_2$)$_n$-Q, wherein n is 0, 1 or 2 and Q is substituted or unsubstituted and is one of: methyl, phenyl, furyl, thienyl, and pyridinyl.

In another embodiment, Q is methyl.

In another embodiment, Q is phenyl, furyl, thienyl or pyridinyl having from 0 to 2 substituents, said substituents being selected from F, Cl, Br, I, CF$_3$, CH$_3$, ethyl, isopropyl, OH, and OCH$_3$.

In another embodiment, A is thienyl, furyl, pyridinyl, oxazolyl, thiazolyl, or imidazolyl having 1 or 2 substituents, said substituents being selected from F, Cl, Br, I, CF$_3$, CH$_3$, ethyl, isopropyl, OH, and OCH$_3$.

In another embodiment, A is thienyl, furyl, pyridinyl, oxazolyl, thiazolyl, or imidazolyl having 1 or 2 substituents, said substituents being selected from F, Cl, Br, I, CF$_3$, CH$_3$, ethyl, isopropyl, OH, and OCH$_3$.

Another embodiment is a compound represented by the formula:

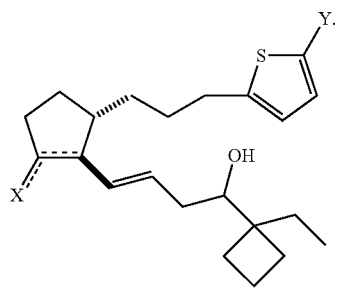

wherein Y is a carboxylic acid or an amide or ester thereof having from 0 to 14 carbon atoms.

Another embodiment is a compound represented by the formula:

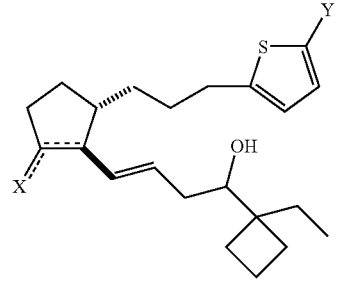

wherein Y is CO$_2$(CH$_2$)$_2$OH, or

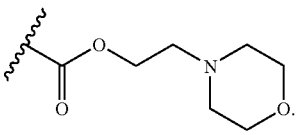 [SMILES: *C(=O)OCCN1CCOCC1]

Another embodiment is a compound selected from:

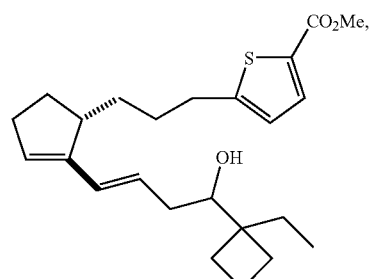

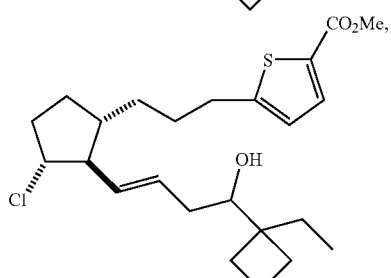

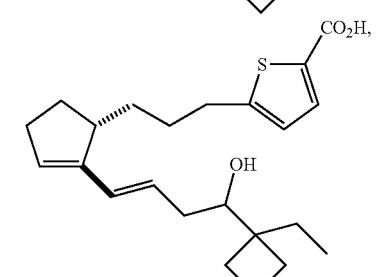

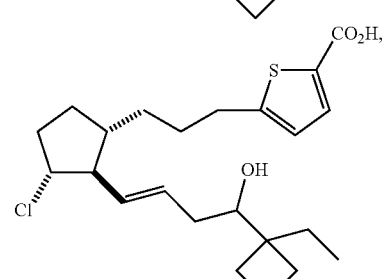

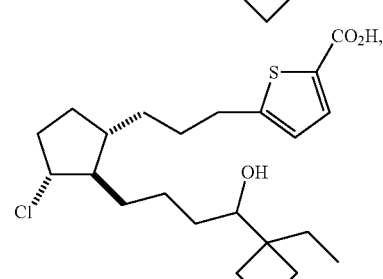

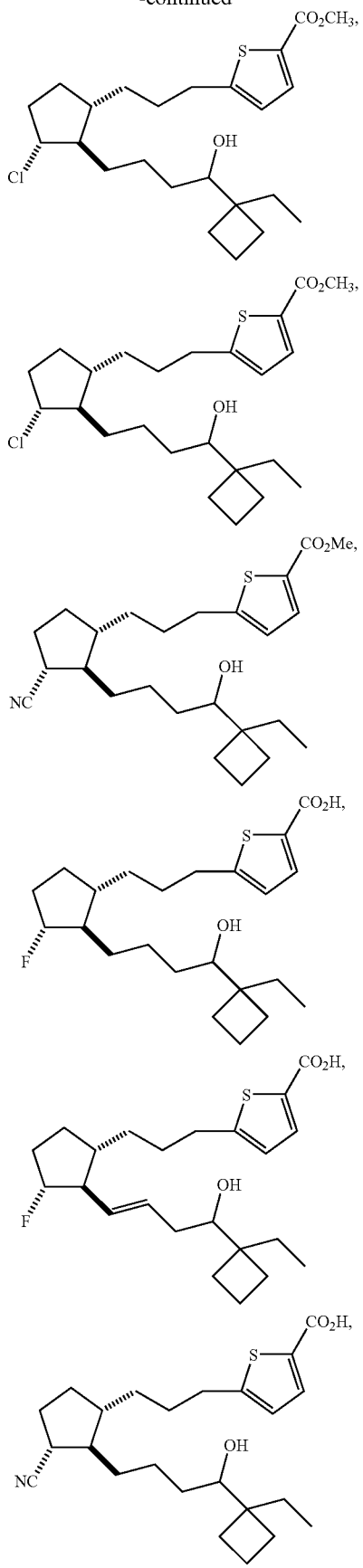
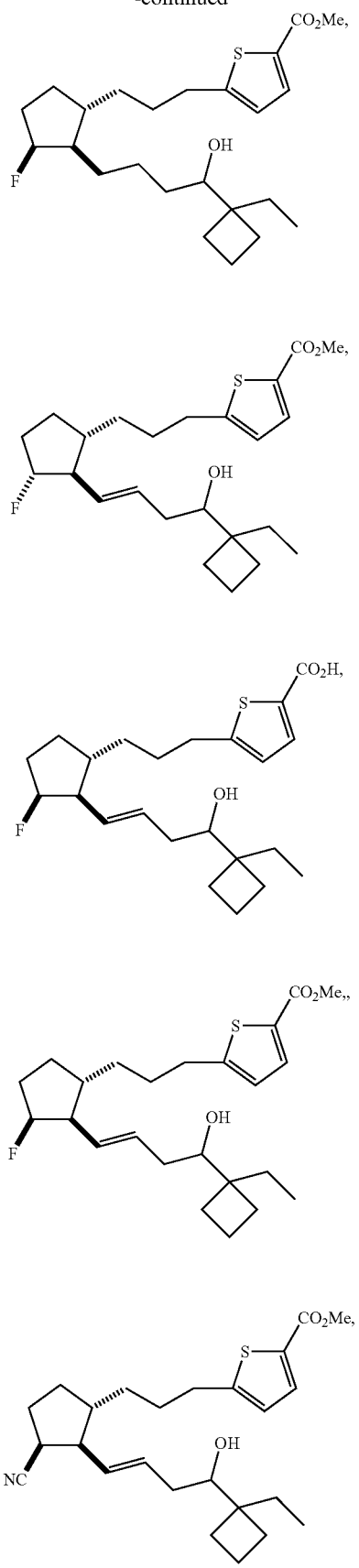

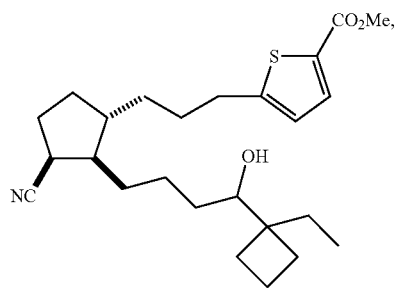
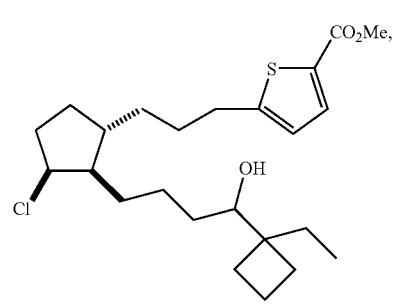
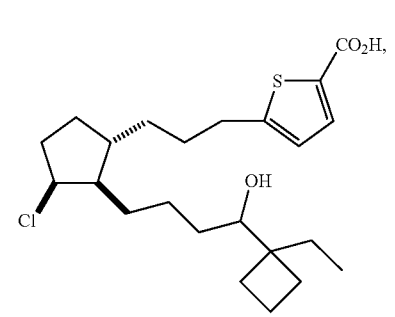
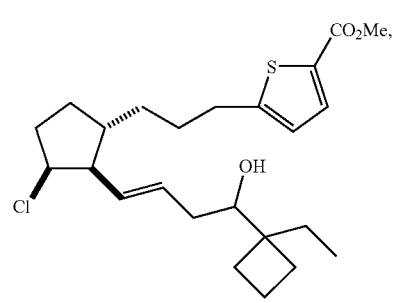
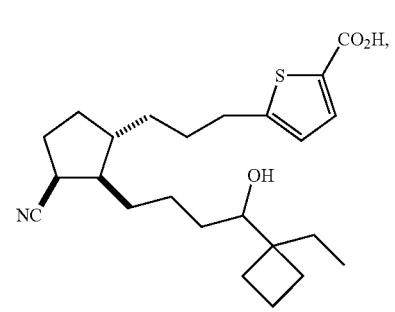
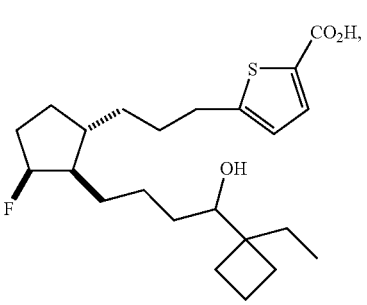
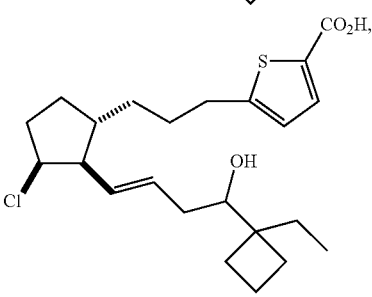
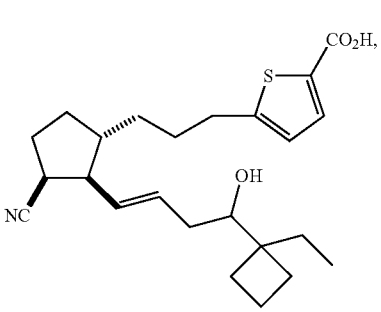
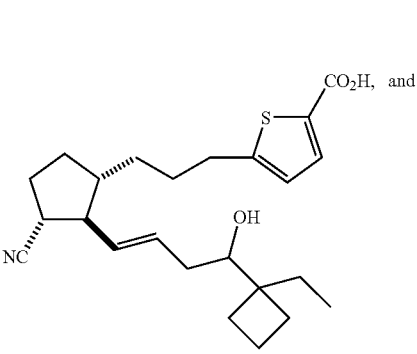
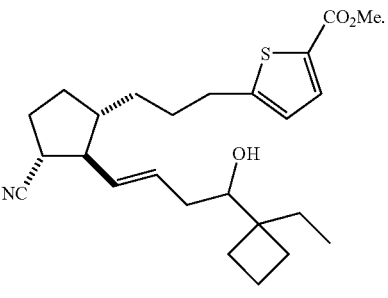

Synthetic Methods
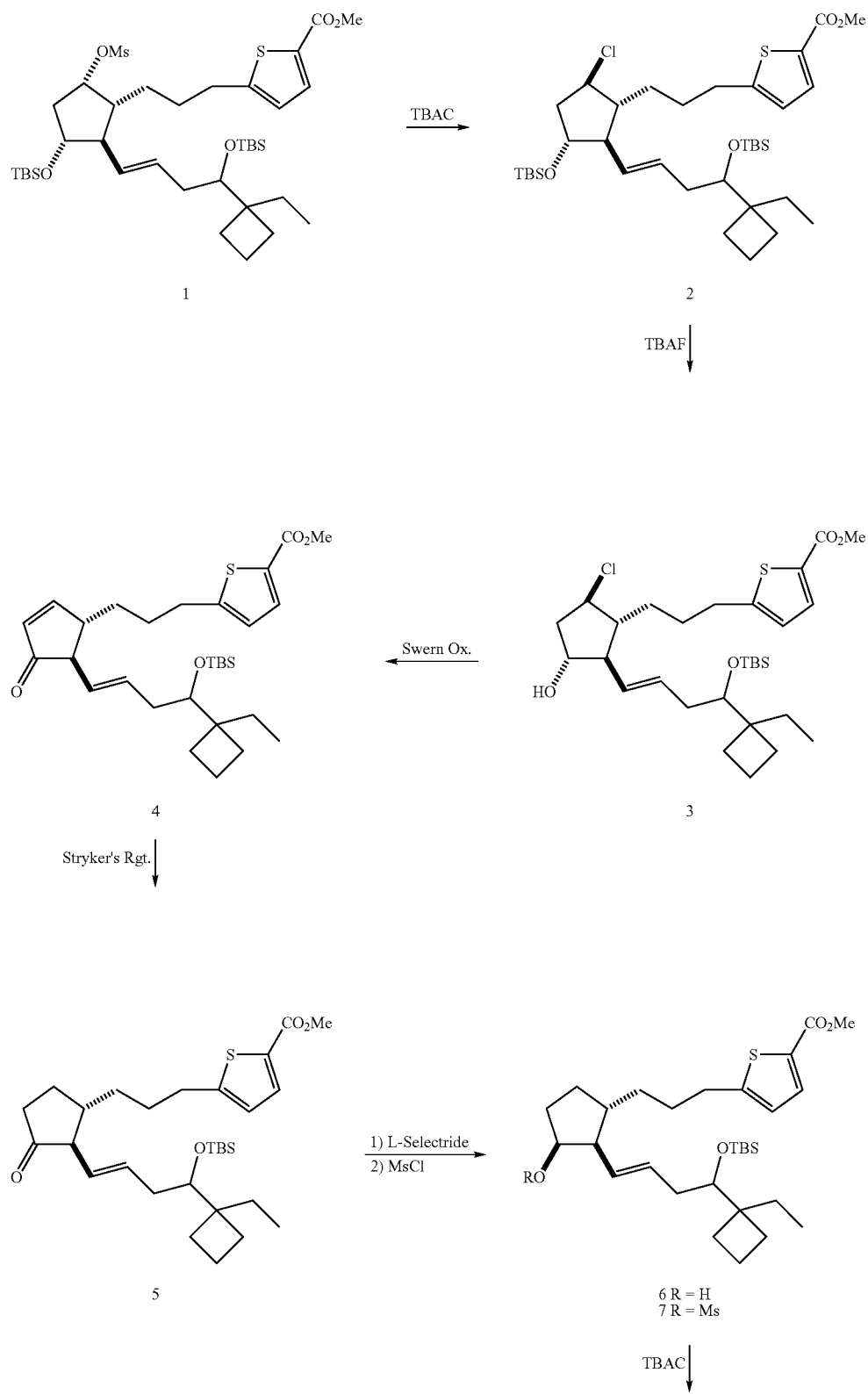

-continued

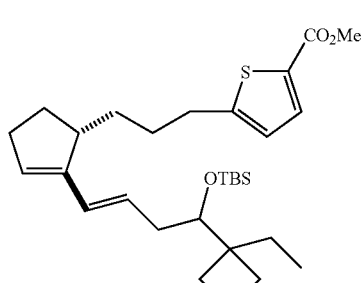

14

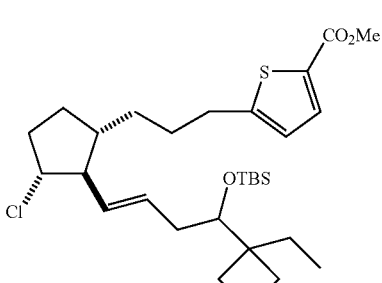

8

HF·pyr ↓      HF·pyr ↓

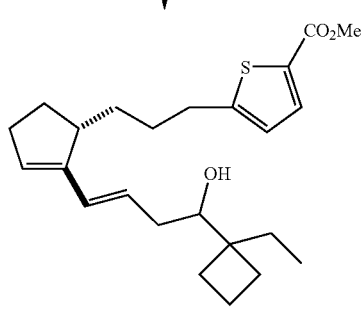

15

9

LiOH ↓      LiOH ↓

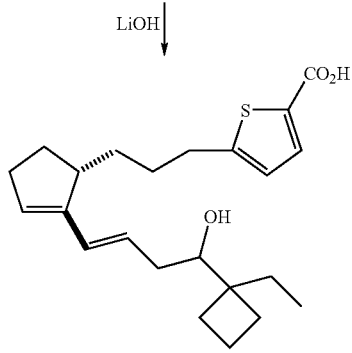

16

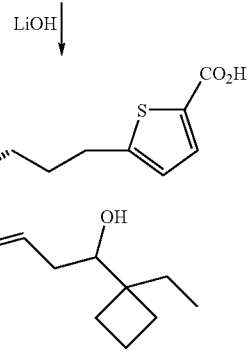

10

The examples herein illustrate methods that may be used to synthesize these compounds, but others may be used. In this example, a compound such as 1 in Scheme 1 is obtained by adapting methods described in Kousuke, T. et al. *Bioorg. Med. Chem.* 2002, 10, 1093 and U.S. provisional patent application No. 60/869,468, filed on Dec. 11, 2006.

Compound 2.

TBAC (839 mg, 3.0 mmol) was added a solution of mesylate 1 (473 mg, 0.6 mmol) in 20 mL toluene. The mixture was then stirred at 45° C. for 6 hours, at which time another portion of TBAC (3 equivalents) was added. After stirring another 14 hours at 45° C., the mixture was cooled to room temperature and water was added. The toluene layer was separated and the aqueous layer was extracted 3x with EtOAc. The combined organics were washed with brine, dried ($Na_2SO_4$) and concentrated. Flash chromatography (FCC) provided chloride 2 (320 mg).

Compound 3.

TBAF (0.44 mL, 0.44 mmol; 1M in THF) was added to a solution of 2 (300 mg, 0.44 mmol) in THF (5 mL) and the mixture was stirred at rt. After 30 min, additional TBAF (0.1 mL, 0.1 mmol) was added, followed by the addition of more TBAF (0.1 mL, 0.1 mmol) 20 minutes later. After no further change was observed by TLC, water and brine was added and the aqueous phase was extracted with EtOAc (3x). The combined organics were dried ($Na_2SO_4$) and concentrated. FCC provided 220 mg of alcohol 3.

Compound 4.

DMSO (0.15 mL, 2.11 mmol) was added to a solution of oxalyl chloride (0.528 mL, 1.0 mmol) in $CH_2Cl_2$ (20 mL), at −78° C. After 15 min, a solution of alcohol 3 (300 mg, 0.528 mmol) in $CH_2Cl_2$ (5 mL) was added, and the mixture stirred for 1 hour at −78° C. $Et_3N$ (0.588 mL, 4.22 mmol) was added and the reaction was allowed to warm to rt. After 5 hours, the mixture was poured into $NaHCO_3$ (sat), and the mixture was extracted with $CH_2Cl_2$ (3x). The combined organics were washed with HCl (dil), $NaHCO_3$ (sat), brine, and dried ($Na_2SO_4$), and concentrated. FCC afforded 244 mg of enone 4.

Compound 5.

Stryker's Reagent (675 mg, 0.34 mmol) was added to a solution of enone 4 (244 mg, 0.459 mmol) in toluene (10 mL) at −40° C. After stirring 2 hours, the reaction was warmed to room temperature and stirred an additional 16 hours. The mixture was then quenched with a 5:1 mixture of $NH_4Cl$ (sat)/$NH_4OH$ and stirring continued another 30 min. The mixture was then extracted with EtOAc and $CH_2Cl_2$. The combined organics were dried ($Na_2SO_4$), concentrated, and FCC gave 130 mg of ketone 5.

Compound 6.

L-Selectride (0.188 mL, 0.188 mmol) was added to a solution of ketone 5 (50 mg, 0.094 mmol) in THF (2 mL) at −78° C. After 30 minutes of stirring, 3% $H_2O_2$ (4.4 mL) was added and the reaction was warmed to rt. After 1 hour of stirring at rt, $NH_4Cl$ (sat) was added and the mixture was extracted with EtOAc (3x). The combined organics were washed with brine, dried ($Na_2SO_4$), concentrated, and FCC gave 30 mg of the desired alcohol 6.

Compound 7.

Mesyl Chloride (0.01 mL) was added to a solution of alcohol 6 (30 mg, 0.056 mmol) and $Et_3N$ (0.022 mL, 0.159 mmol) in $CH_2Cl$ (1 mL). After stirring 2 hours at rt, the mixture was concentrated and FCC provided 28 mg of mesylate 7.

Compound 8.

TBAC (63 mg, 0.228 mmol) was added to a solution of mesylate 7 (28 mg, 0.046 mmol) in toluene (5 mL). The mixture was stirred at 40° C. for 16 hours, and TLC revealed the presence of starting material. An additional portion of TBAC (63 mg, 0.228 mmol) was added and stirring at 40° C. was continued for an additional 20 hours. The reaction was cooled to rt, quenched with water, and extracted with EtOAc (3x). The combined organics were washed with brine, dried ($Na_2SO_4$) and FCC followed by HPLC provided 5 mg of the elimination product alkene 14, and 10 mg of chloride 8.

Compound 9.

HF pyr (0.2 mL) was added to a solution of chloride 8 (10 mg 0.018 mmol) in MeCN (2 mL) in a plastic vial. After stirring 4 hours, the mixture was quenched with $NaHCO_3$ (sat), and extracted with EtOAc (3x). The combined organics were washed with copper sulfate (sat), brine, and dried ($Na_2SO_4$). FCC afforded alcohol 9.

Compound 10.

LiOH (3 mg, 0.071 mmol) was added to a solution of ester 9 (3 mg, 0.068 mmol) in a 1:1 THF/water solution (2 mL). After having stirred 48 h, FCC provided 2.3 mg of acid 10.

Compound 15.

The procedure of Example 9 was employed with alkene 14 (5 mg, 0.0096 mmol) to afford 2 mg of alcohol 15.

Compound 16.

The procedure of Example 10 was employed with alcohol 15 (2 mg, 0.0049 mmol) to afford 2 mg of acid 16.

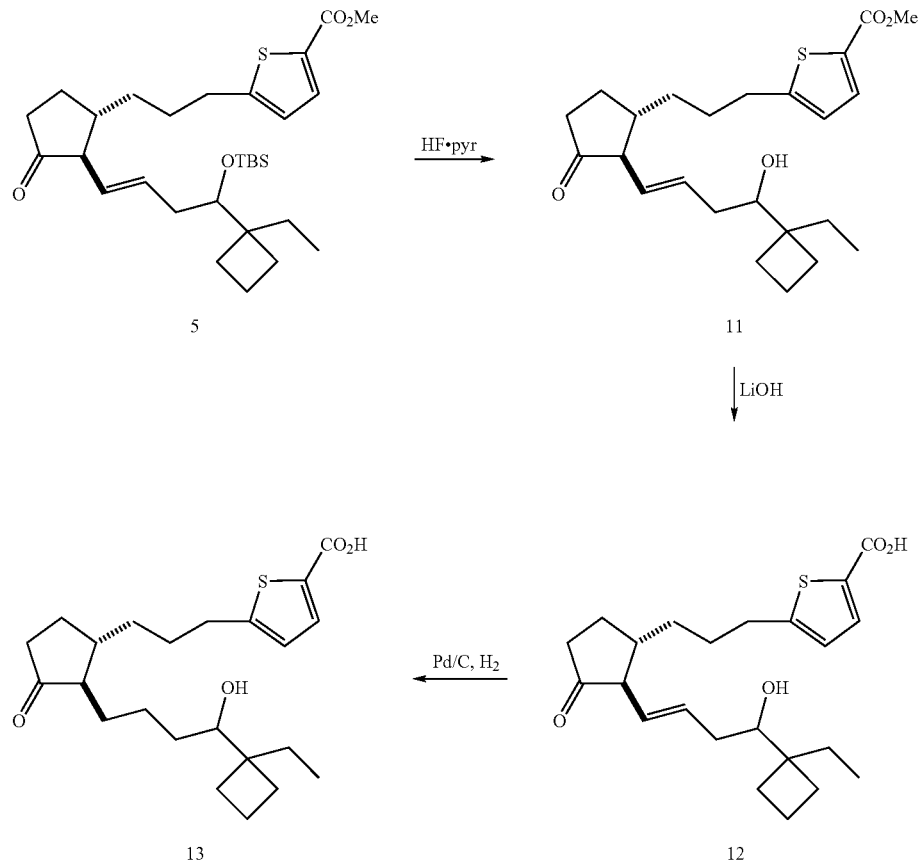

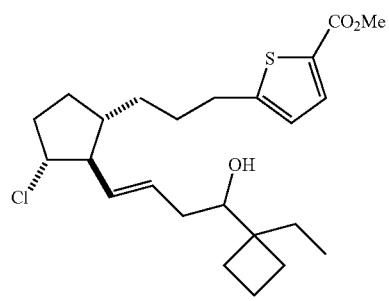

9

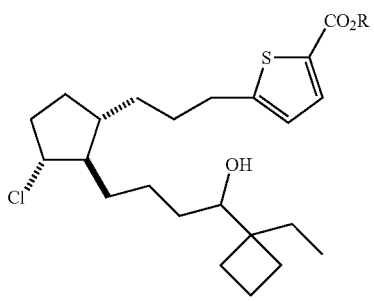

66 R = Me
67 R = H

Compound 11.
The procedure of Example 9 was employed with ketone 5 (30 mg, 0.056 mmol) to afford 15 mg of alcohol 11.

Compound 12.
To a solution of ester 11 (5 mg, 0.012 mmol), MeCN (0.2 mL), and pH 7.2 phosphate buffer (2 mL) was added Rabbit Liver Esterase (1K units, 1 mmol). The mixture stirred at room temperature for 3 days and FCC then provided 2 mg of acid 12.

Compound 13.

To a stirred mixture of alkene 12 and MeOH (2 mL), was added 5% Pd/C (1 mg). The flask was then placed under an atmosphere of $H_2$ (g) and the reaction was stirred for 16 hours. The mixture was then concentrated and FCC provided 0.8 mg of acid 13.

Scheme 3

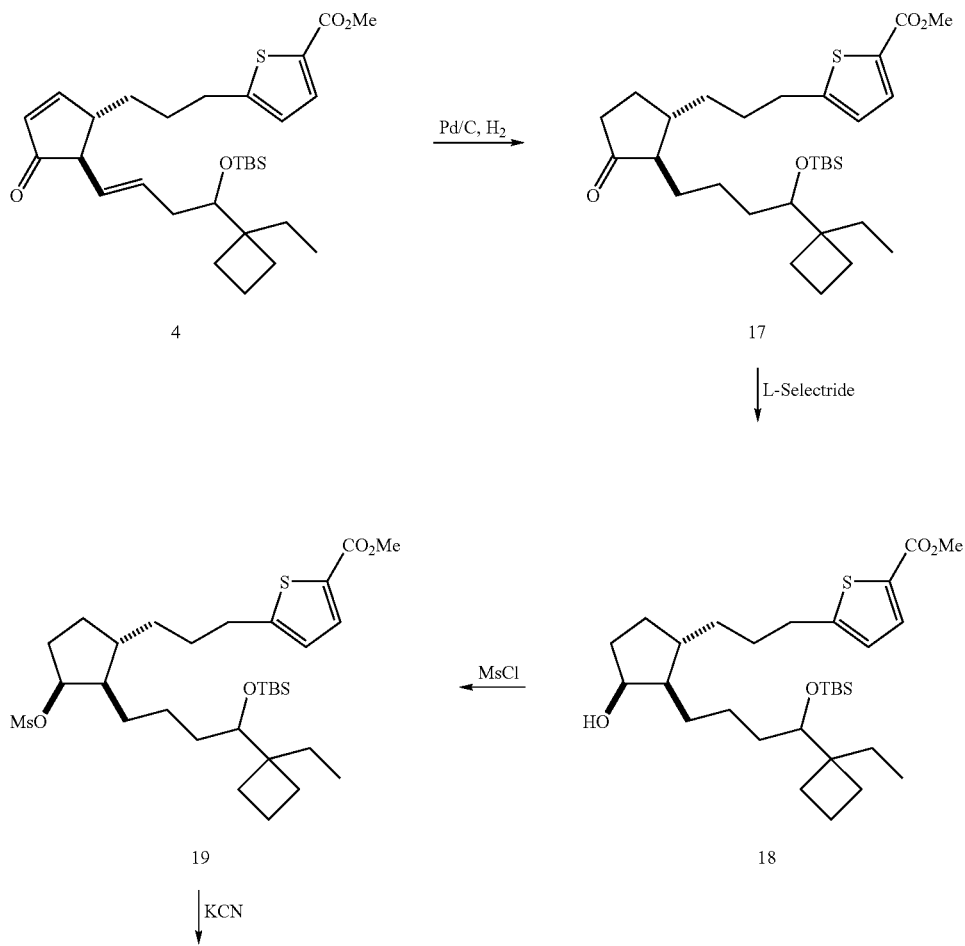

27                                28

-continued

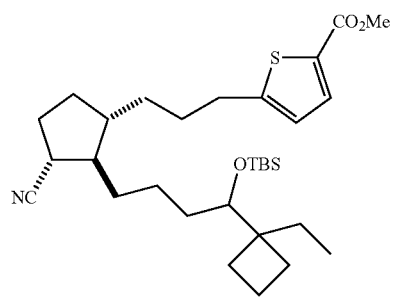
20

HF·pyr →

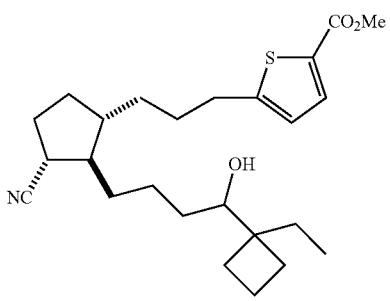
21

↓ LiOH

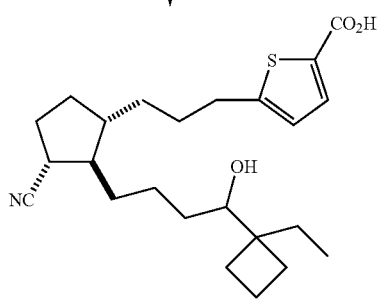
22

Compound 17.
The procedure of Example 13 was employed with enone 4 (1.2 mg, 2.9 μmol) to afford 0.6 mg of ketone 17.

Compound 18.
The procedure of Example 6 was employed with ketone 17 (65 mg, 0.122 mmol) to afford 51 mg of alcohol 18.

Compound 19.
The procedure of Example 7 was employed with alcohol 18 (51 mg, 0.096 mmol) to afford 43 mg of mesylate 19.

Compound 20.
KCN (8 mg, 0.13 mmol) was added to a solution of mesylate 19 (8 mg, 0.013 mmol) in DMSO (2 mL), and the mixture was then brought to 70° C. and stirred for 20 hours. The mixture was then cooled to rt, diluted with water/brine, and extracted with EtOAc (3x). The combined organics were washed with brine, dried (Na$_2$SO$_4$) and Combiflash to provide 3 mg of nitrile 20.

Compound 21.
The procedure of Example 9 was employed with nitrile 20 (3 mg, 0.0055 mmol) to afford 1.5 mg of alcohol 21.

Compound 22.
The procedure of Example 10 was employed with alcohol 21 (1.5 mg, 0.0035 mmol) to afford 0.8 mg of acid 22.

Scheme 4

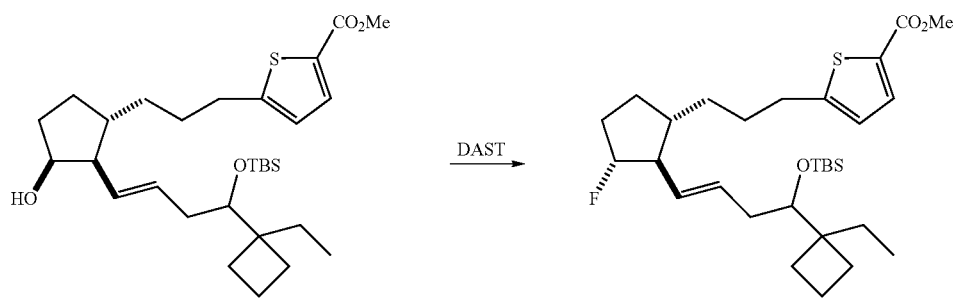

↓ HF·pyr

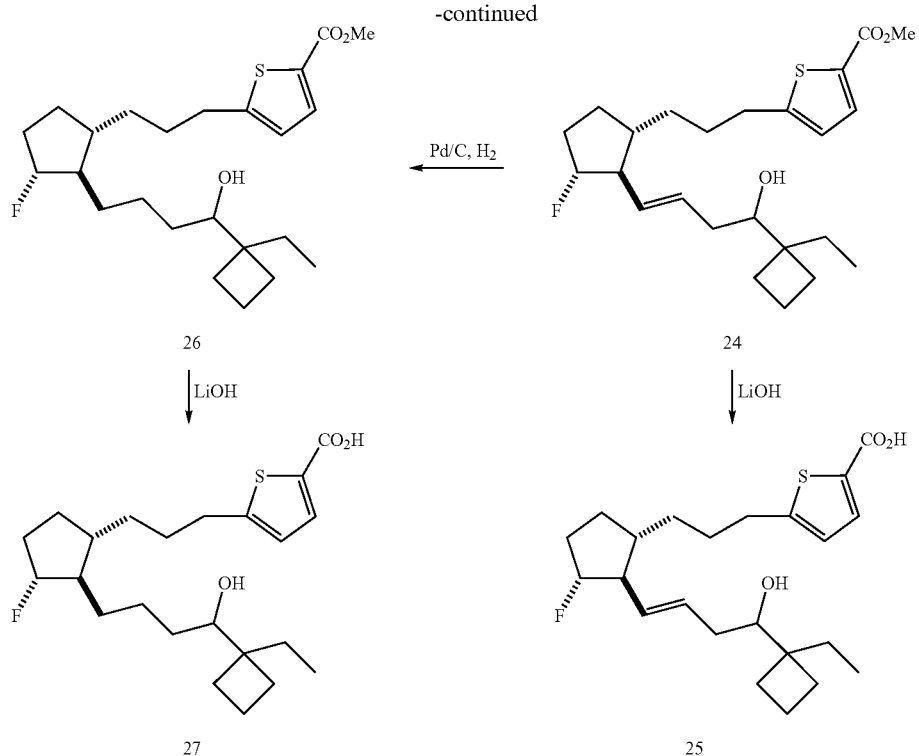

Compound 23.

DAST (19 μL, 0.15 mmol) was added to a solution of alcohol 6 (40 mg, 0.075 mmol) in CH₂Cl₂ (2 mL) at −78° C. After stirring for 30 minutes, the mixture was diluted with water, extracted with CH₂Cl₂ (3x), hexanes (1x), and the combined organics were washed with brine and dried Na₂SO₄. Combiflash provided 10 mg of fluoride 23 and 14 mg of diene 28.

Compound 24.

The procedure of Example 9 was employed with fluoride 23 (10 mg, 0.0186 mmol) to afford 7 mg of alcohol 24.

Compound 25.

The procedure of Example 10 was employed with alcohol 24 (7 mg, 0.017 mmol) to afford 6 mg of acid 25.

Compound 26.

The procedure of Example 13 was employed with alkene 24 (2 mg, 0.005 mmol) to afford 2 mg of fluoride 26.

Compound 27.

The procedure of Example 10 was employed with alcohol 26 (2 mg, 0.005 mmol) to afford 0.5 mg of acid 27.

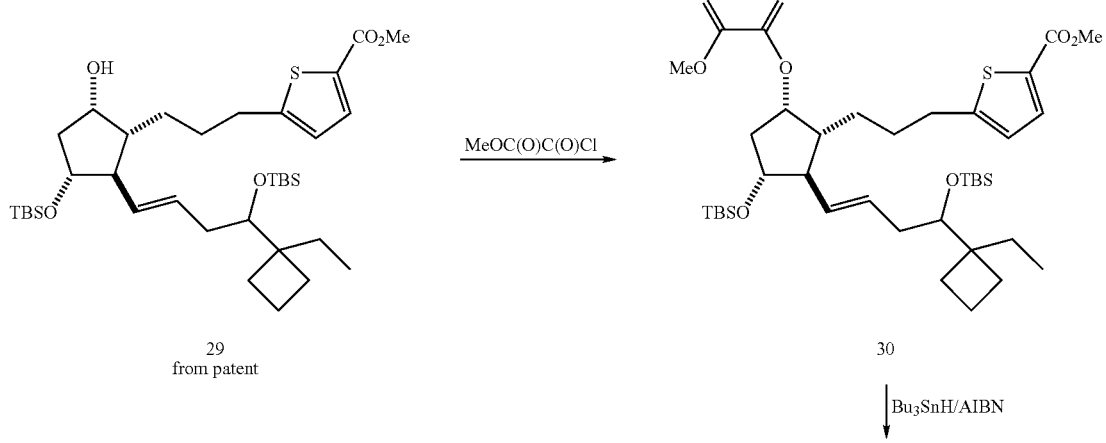

31

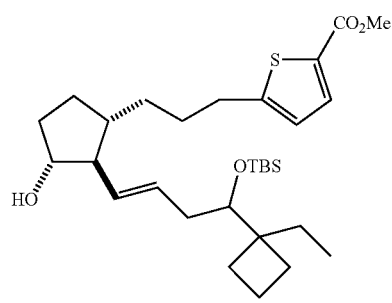

32

32

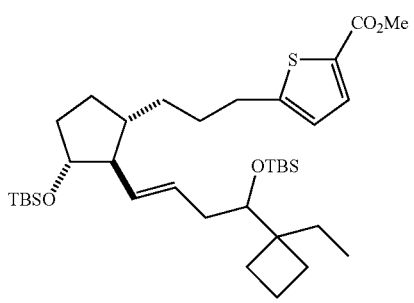

31

TBAF ←

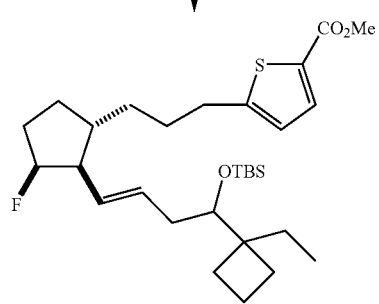

33

DAST ↓

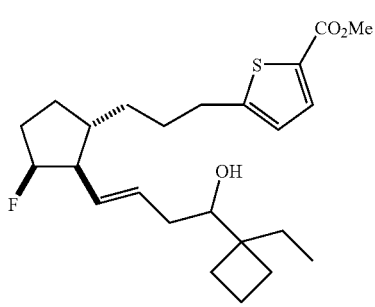

34

HF·pyr →

Pd/C, H₂ ↙          ↓ LiOH

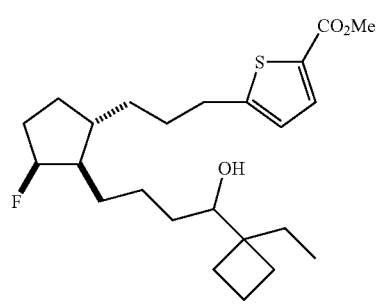

36

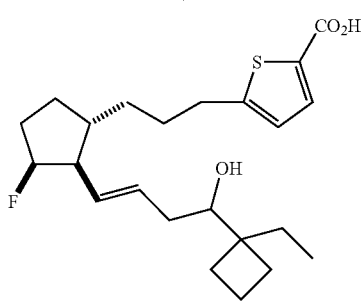

35

LiOH ↓

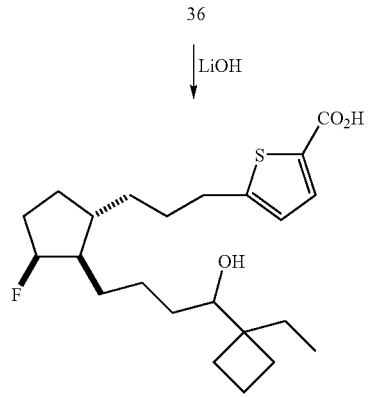

37

Compound 30.

Methyl oxalyl chloride was added slowly to a mixture of alcohol 29 (1.3 g, 1.95 mmol), pyridine (1.6 mL), 4-DMAP (714 mg), and CH₂Cl₂ (3 mL). After 1 hour, the mixture was quenched with water, diluted with brine, and extracted with EtOAc/hexanes (5:1). The organic phase was washed again with a water/brine mixture (2:1), brine, and dried (Na₂SO₄). Combiflash afforded 1.32 g of ester 30.

Compound 31.

A mixture of oxalyl ester 30 (1.32 g, 1.76 mmol), AIBN (285 mg) and toluene (25 mL) was bubbled with Nitrogen (g) for 20 min. Seperately, a solution of Bu$_3$SnH (4.1 g, 14 mmol) in toluene (100 mL) was bubbled with Nitrogen (g) for 20 min, and then brought to 120° C. The AIBN containing mixture was quickly added dropwise. After 20 min, TLC indicated no starting material and the reaction was concentrated. Combiflash provided ester 31.

Compound 32.

The procedure of Example 3 was employed with ester 31 (420 mg, 3.9 mmol) to afford 260 mg of alcohol 32.

Compound 33.

The procedure of Example 23 was employed with ester 32 (20 mg, 0.037 mmol) to afford 13 mg of fluoride 33.

Compound 34.

The procedure of Example 9 was employed with fluoride 33 (13 mg, 0.024 mmol) to afford 3.8 mg of alcohol 34.

Compound 35.

The procedure of Example 10 was employed with alcohol 34 (3.8 mg, 0.0049 mmol) to afford 1 mg of acid 35.

Compound 36.

The procedure of Example 13 was employed with alkene 34 (2 mg, 0.005 mol) to afford 1.5 mg of fluoride 36.

Compound 37.

The procedure of Example 10 was employed with fluoride 36 (1.5 mg, 0.004 mmol) to afford 0.9 mg of acid 37.

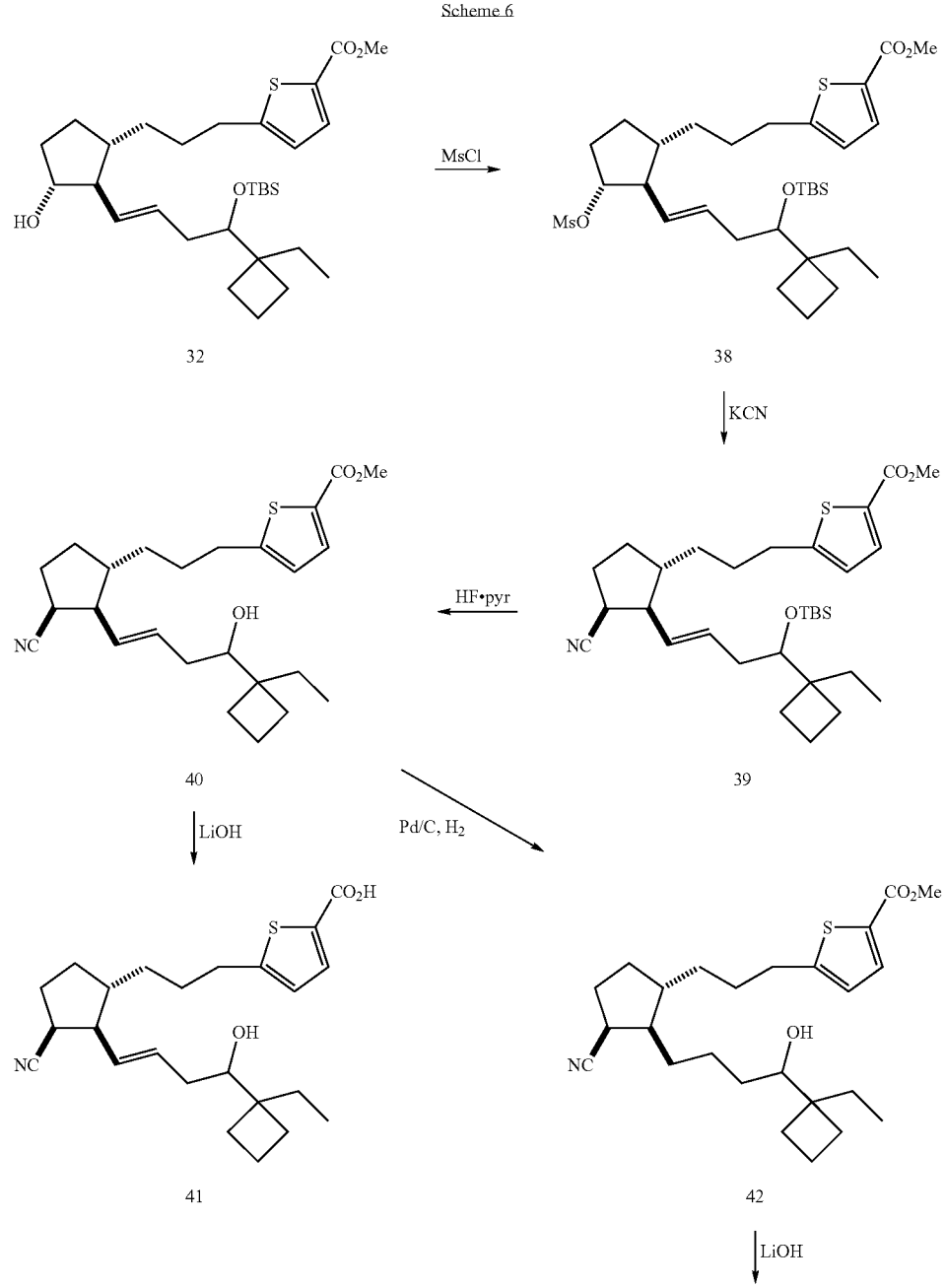

Scheme 6

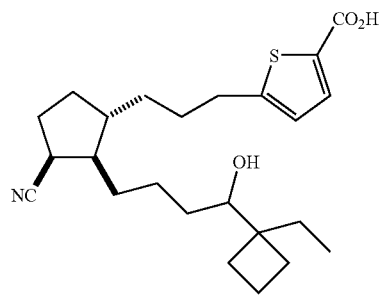

43

Compound 38.
The procedure of Example 7 was employed with alcohol 32 (45 mg, 0.084 mmol) to afford 41 mg of mesylate 38.

Compound 39.
The procedure of Example 20 was employed with mesylate 38 (20 mg, 0.033 mmol) to afford 6 mg of nitrile 39.

Compound 40.
The procedure of Example 9 was employed with nitrile 39 (6 mg, 0.01 mmol) to afford 4.2 mg of alcohol 40.

Compound 41.
The procedure of Example 10 was employed with alcohol 40 (2.2 mg, 0.005 mmol) to afford 1.6 mg of acid 41.

Compound 42.
The procedure of Example 13 was employed withh alkene 40 (2 mg, 0.005 mol) to afford 1.8 mg of nitrile 42.

Compound 43.
The procedure of Example 10 was employed with ester 42 (1.8 mg, 0.0041 mmol) to afford 1.7 mg of acid 43.

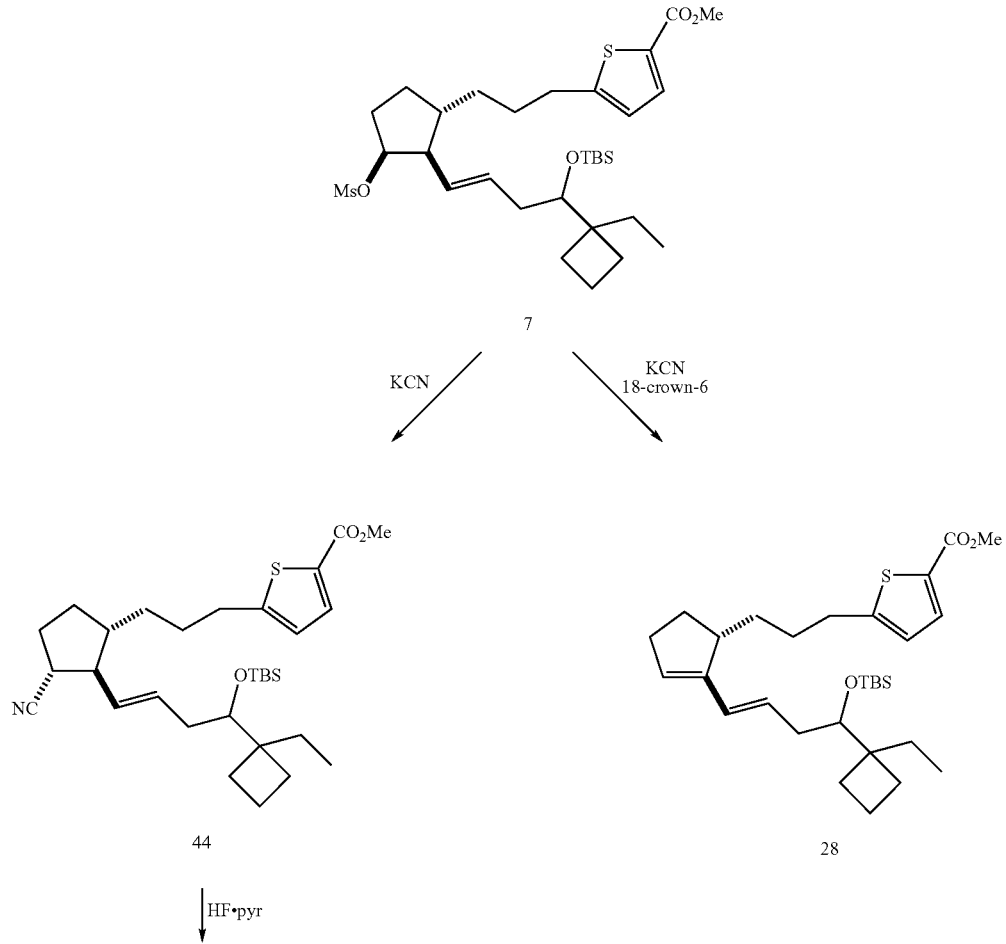

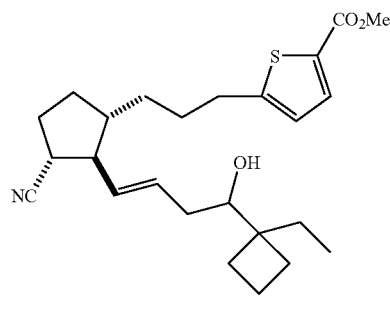

45

↓ LiOH

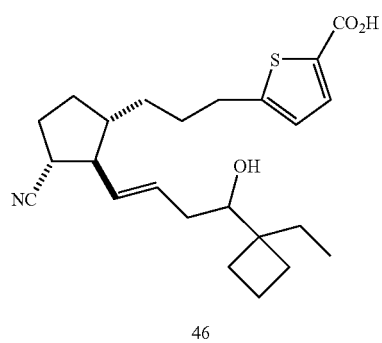

46

Compound 28.

KCN (13 mg, 0.21 mmol) was added to a solution of mesylate 7 (43 mg, 0.14 mmol) and 18-crown-6 (37 mg, 0.14 mmol) in DMSO (5 mL), and the mixture was then brought to 65° C. and stirred for 16 hours. The mixture was then cooled to rt, diluted with water/brine, and extracted with CHCl₃ (x4) EtOAc (3x). The combined organics were dried (Na₂SO₄) and FCC provided 14 mg of diene 28.

Compound 44.

The procedure of Example 20 was employed with mesylate 7 (120 mg, 0.195 mmol) to afford 77 mg of nitrile 44.

The procedure of Example 9 was employed with alkene 44 (77 mg, 0.141 mmol) to afford 5.7 mg of alcohol 45.

Compound 46.

The procedure of Example 10 was employed with alcohol 45 (5 mg, 0.017 mmol) to afford 2.5 mg of acid 46.

Scheme 8

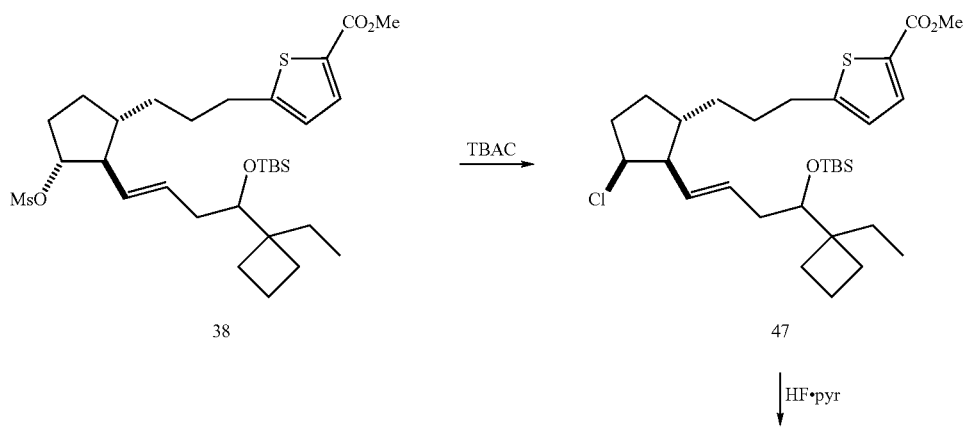

↓ HF•pyr

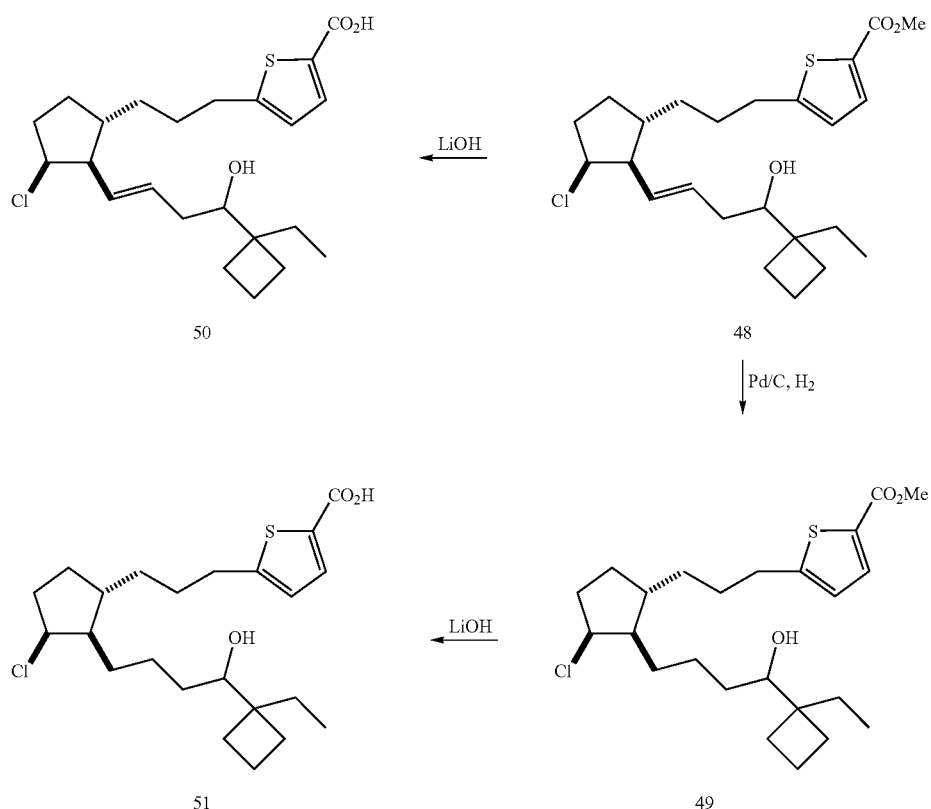

Compound 47.

The procedure of Example 2 was employed with mesylate 38 (19 mg, 0.031 mmol) to afford 12.5 mg of chloride 47.

Compound 48.

The procedure of Example 9 was employed with alkene 47 (12.5 mg, 0.141 mmol) to afford 9 mg of alcohol 48.

Compound 49.

The procedure of Example 13 was employed with alcohol 48 (5 mg, 0.017 mmol) to afford 3.4 mg of acid 49.

Compound 50.

The procedure of Example 10 was employed with alkene 48 (4 mg, 0.01 mmol) to afford 2.4 mg of chloride 50.

Compound 51.

The procedure of Example 10 was employed with alcohol 49 (2.4 mg, 0.0049 mmol) to afford 1.2 mg of acid 51.

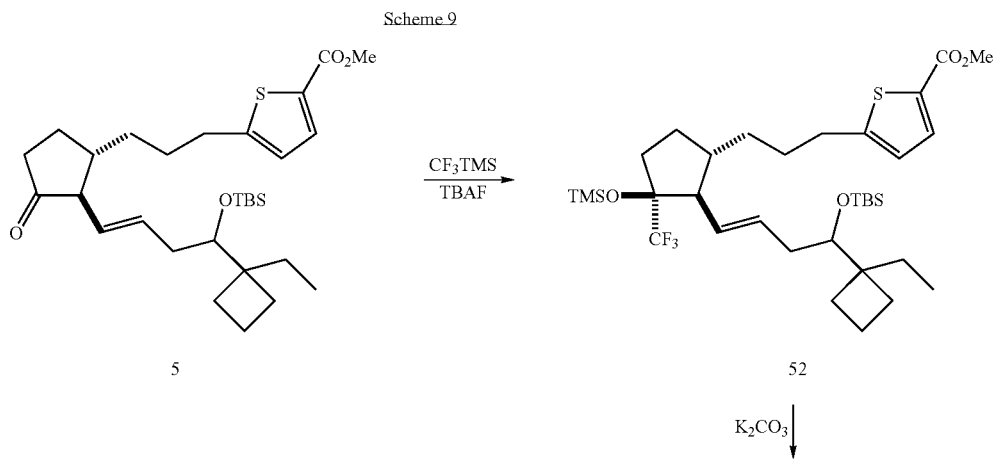

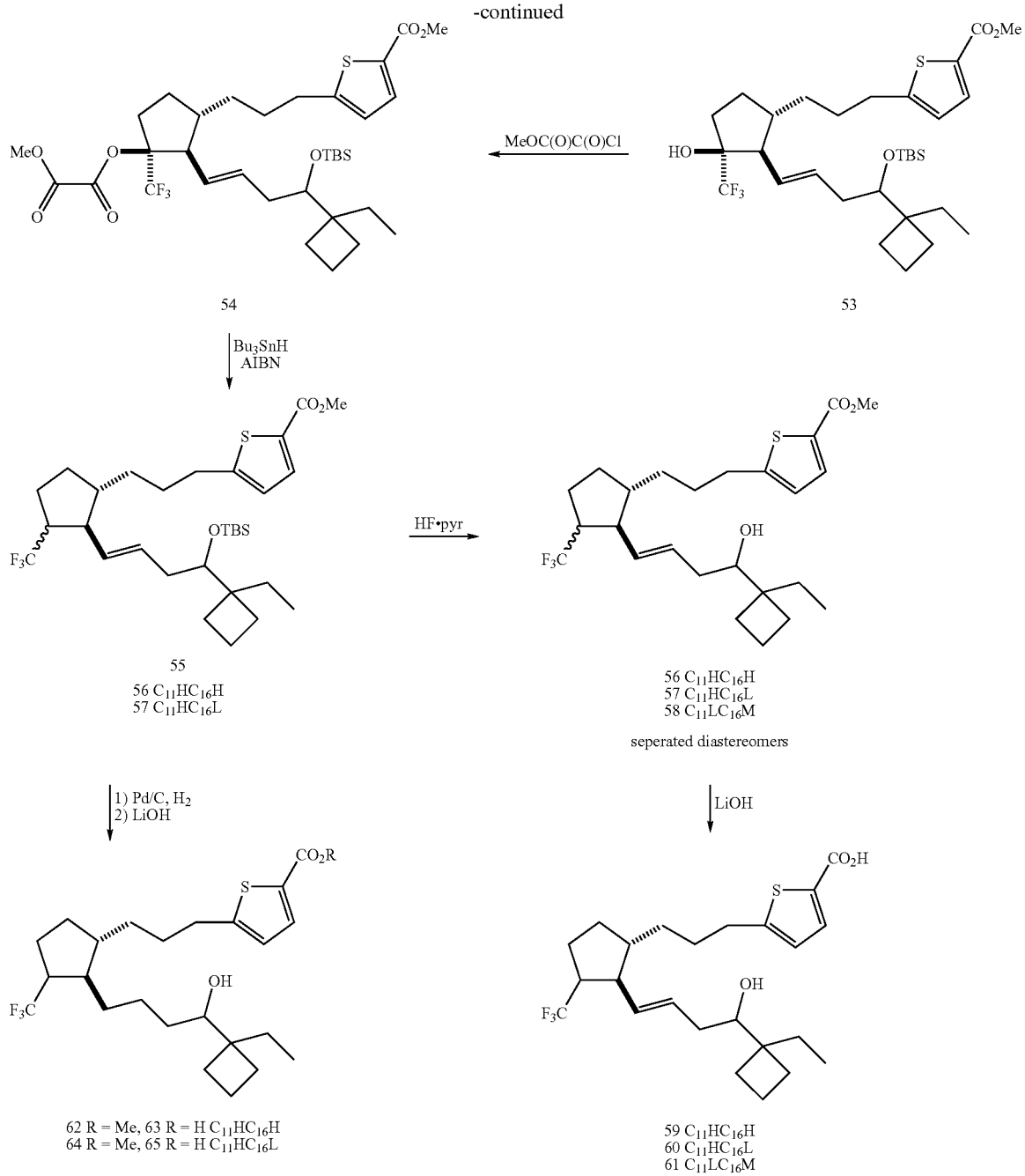

Compound 52.

Trifluoromethyl trimethylsilane (0.94 mL, 1.8 mmol) was added to a solution of ketone 5 (50 mg, 0.094 mmol) in THF (2 mL) at rt, followed by the addition of 2 drops of TBAF (1M in THF); the reaction turned light yellow. Several minutes later, the reaction turned brown and TLC indicated total consumption of starting material. The reaction was quenched slowly with NH$_4$Cl (sat), and extracted with EtOAc (3x). The combined organics were washed with brine, dried (Na$_2$SO$_4$) and concentrated. The crude silane 52 was dried under high vacuum for 4 hours prior to the following reaction.

Compound 53.

Solid K$_2$CO$_3$ (39 mg, 0.283 mmol) was added to crude silane 52 in MeOH (2 mL) and the mixture was stirred for four hours. The reaction was then diluted with NH$_4$Cl (sat), extracted with EtOAc, and the organic phase was washed with brine, dried (Na$_2$SO$_4$) and concentrated. Combiflash 56 mg of alcohol 53.

Compound 54.

Methyl oxalyl chloride (57 mg, 0.465 mmol) was added slowly to a mixture of alcohol 53 (56 mg, 0.093 mmol), pyridine (0.225 mL), 4-DMAP (68 mg), and CH$_2$Cl$_2$ (2 mL). After 1 hour, the mixture was quenched with water, diluted with brine, and extracted with EtOAc/hexanes (5:1). The organic phase was washed again with a water/brine mixture (2:1), brine, and dried (Na$_2$SO$_4$). Combiflash afforded 34 g of ester 54.

43

Compound 55.

A mixture of oxalyl ester 54 (34 mg, 0.049 mmol), AIBN (8 mg) and toluene (3 mL) was bubbled with Nitrogen (g) for 20 min. Seperately, a solution of $Bu_3SnH$ (4.1 g, 14 mmol) in toluene (4 mL) was bubbled with Nitrogen (g) for 20 min, and then brought to 120° C. The AIBN containing mixture was quickly added dropwise. After 20 min, TLC indicated no starting material and the reaction was concentrated. Combiflash provided 1 lmg ester 55.

Compound 56.

The procedure of Example 9 was employed with alkene 55 (11 mg, 0.019 mmol) to afford 2.6 mg of alcohol 56, 2.5 mg of alcohol 57, and 1.9 mg of alcohol 58.

Compound 59.

The procedure of Example 10 was employed with alcohol 56 (2.6 mg, 0.0054 mmol) to afford 1.2 mg of acid 59.

Compound 60.

The procedure of Example 10 was employed with alcohol 57 (2.5 mg, 0.0053 mmol) to afford 1.6 mg of acid 60.

Compound 61.

The procedure of Example 10 was employed with alcohol 58 (1.9 mg, 0.004 mmol) to afford 1 mg of acid 61.

Compound 62.

The procedure of Example 13 was employed with alkene 56 (1 mg, 0.0021 mmol) to afford 1 mg of fluoride 62.

Compound 63.

The procedure of Example 10 was employed with alcohol 62 (2 mg, 0.005 mmol) to afford 2 mg of acid 63.

Compound 64.

The procedure of Example 13 was employed with alkene 57 (1 mg, 0.0021 mmol) to afford 1 mg of fluoride 64.

Compound 65.

The procedure of Example 10 was employed with alcohol 64 (2 mg, 0.005 mmol) to afford 1.2 mg of acid 65.

Compound 66.

The procedure of Example 13 was employed with alkene 9 (5 mg, 0.011 mmol) to afford 3 mg of fluoride 66.

Compound 67.

The procedure of Example 10 was employed with alcohol 66 (3 mg, 0.005 mmol) to afford 0.9 mg of acid 67.

In Vitro Testing

United States Patent Application Publication No. 20070129552, describes the methods used to obtain the in vitro data in Table 1 below. The part of that reference which describes the method is incorporated by reference herein.

TABLE 1

| Compound | EP2 cAMP EC$_{50}$ nM | EP2 Binding Ki nM |
|---|---|---|
| 10 | 17, 7 | 31, 16 |
| 12 | 5.4 | 86 |
| 13 | 6.3 | 137 |
| 16 | 32 | 17 |
| 22 | 18 | 123 |
| 25 | 5.7 | 16, 67 |
| 27 | 8.5 | 15, 47 |
| 35 | 23 | 36 |
| 37 | 19 | 25 |
| 41 | 129 | 1388 |
| 43 | 54 | 516 |
| 46 | 2.5 | 32 |
| 50 | 117 | 1168 |
| 51 | 114 | 377 |
| 59 | 18 | 124 |
| 60 | 46 | 141 |
| 61 | 197 | 310 |

TABLE 1-continued

| Compound | EP2 cAMP EC$_{50}$ nM | EP2 Binding Ki nM |
|---|---|---|
| 63 | 67 | 462 |
| 65 | 160 | 106 |
| 67 | 11 | 40 |

The foregoing description details specific methods and compositions that can be employed to practice the present invention, and represents the best mode contemplated. However, it is apparent for one of ordinary skill in the art that further compounds with the desired pharmacological properties can be prepared in an analogous manner, and that the disclosed compounds can also be obtained from different starting compounds via different chemical reactions. Similarly, different pharmaceutical compositions may be prepared and used with substantially the same result. Thus, however detailed the foregoing may appear in text, it should not be construed as limiting the overall scope hereof; rather, the ambit of the present invention is to be governed only by the lawful construction of the appended claims.

The invention claimed is:

1. A compound represented by the formula:

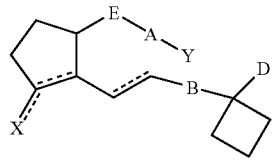

wherein a dashed line represents the presence or absence of a bond;

Y has from 1 to 14 carbon atoms and is:
an organic acid functional group, or
an amide or ester thereof;
hydroxymethyl or an ether thereof; or
a tetrazolyl functional group;

A is aryl or heteroaryl;

E is —$(CH_2)_3$—, cis —$CH_2$—CH=CH—, —O—$(CH_2)_2$, —$CH_2OCH_2$, —$(CH_2)_2O$—, —S—$(CH_2)_2$, —$CH_2SCH_2$, or —$(CH_2)_2S$—;

X is H, F, Cl, Br, I, O, or CN;

B is hydroxyalkyl having from 1 to 5 carbon atoms;

D is —$(CH_2)_n$-Q, wherein n is 0, 1 or 2 and Q is substituted or unsubstituted and is one of: methyl, phenyl, furyl, thienyl, or pyridinyl.

2. The compound of claim 1 wherein Y is a carboxylic acid or an amide or ester thereof having from 1 to 14 carbon atoms.

3. The compound of claim 2 wherein E is —$(CH_2)_3$—, —$(CH_2)_2O$—, or —$(CH_2)_2S$—.

4. The compound of claim 1 wherein Q is methyl.

5. The compound of claim 1 wherein Q is phenyl, furyl, thienyl or pyridinyl having from 0 to 2 substituents, said substituents being selected from F, Cl, Br, I, $CF_3$, $CH_3$, ethyl, isopropyl, OH, and $OCH_3$.

6. The compound of claim 1 wherein A is thienyl, furyl, pyridinyl, oxazolyl, thiazolyl, or imidazolyl having 0, 1 or 2 substituents, said substituents being selected from F, Cl, Br, I, $CF_3$, $CH_3$, ethyl, isopropyl, OH, or $OCH_3$.

7. The compound of claim 1 further represented by the formula:

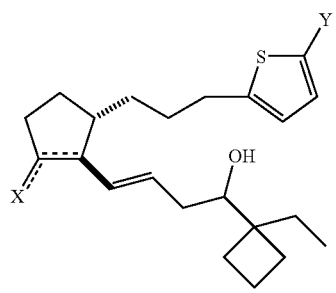
wherein Y is a carboxylic acid or an amide or ester thereof having from 1 to 14 carbon atoms.
8. The compound of claim 7, selected from:
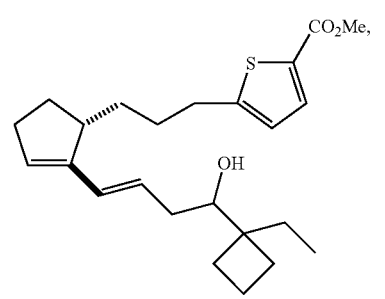
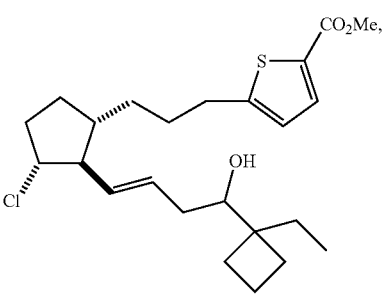
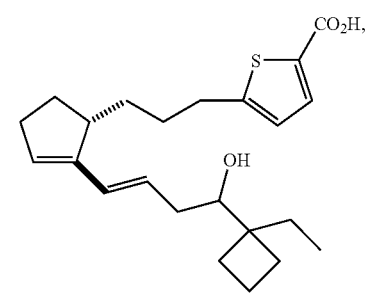
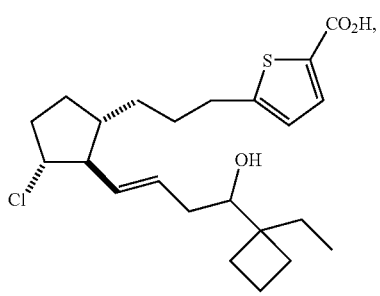
-continued
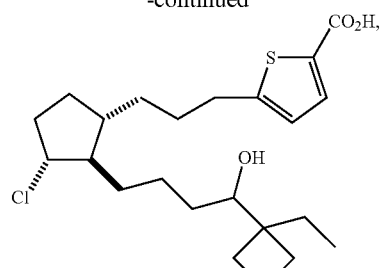
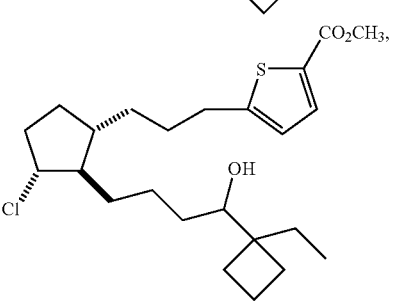
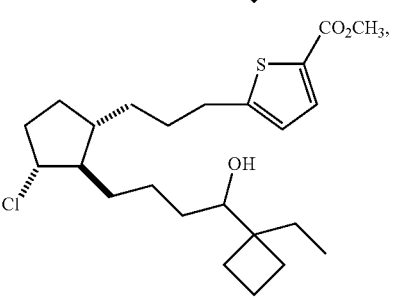
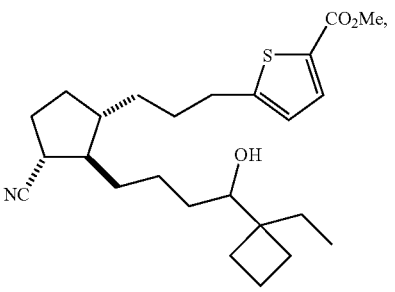
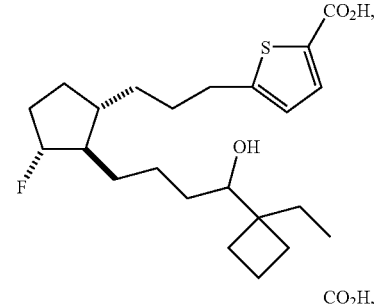
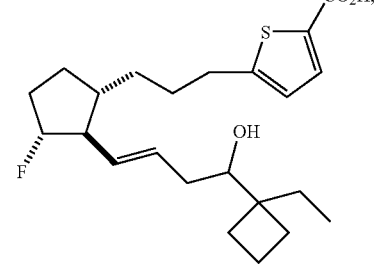

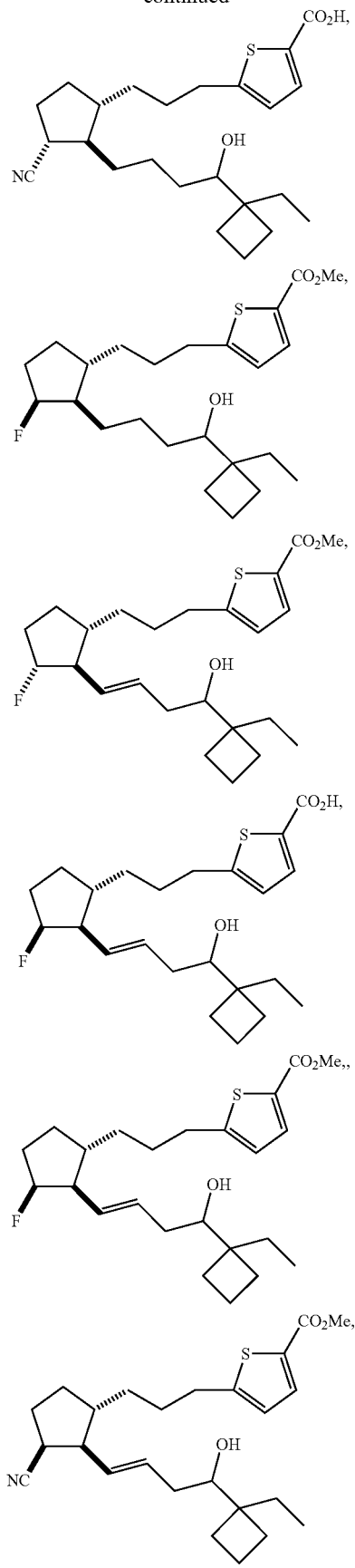
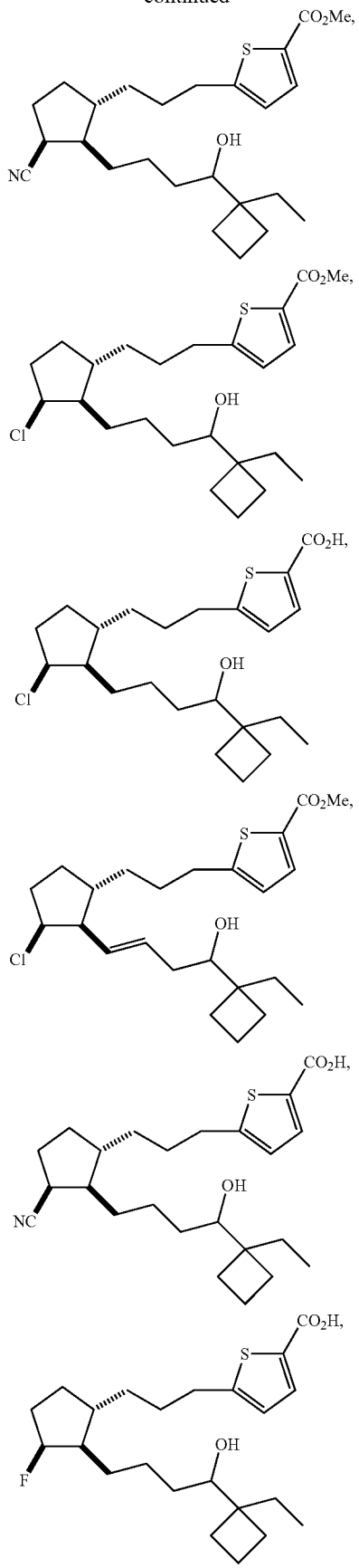

49
-continued
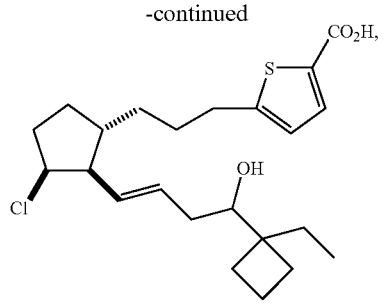
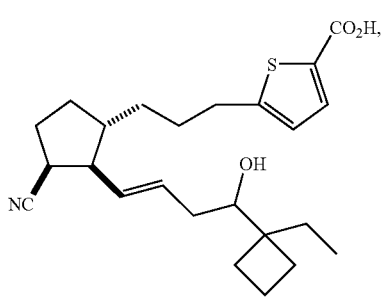
50
-continued
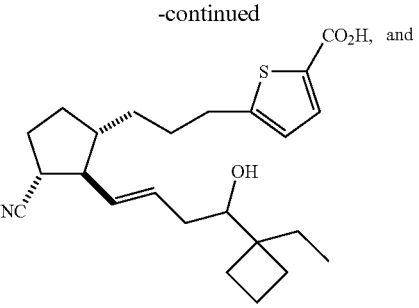
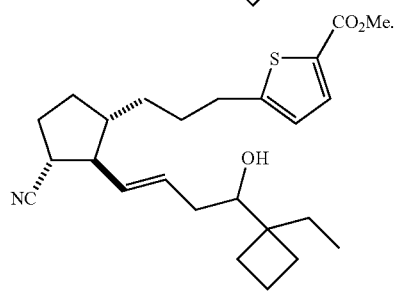
* * * * *

UNITED STATES PATENT AND TRADEMARK OFFICE
CERTIFICATE OF CORRECTION

| | | |
|---|---|---|
| PATENT NO. | : 8,487,091 B2 | Page 1 of 2 |
| APPLICATION NO. | : 12/392571 | |
| DATED | : July 16, 2013 | |
| INVENTOR(S) | : Mark Holoboski et al. | |

It is certified that error appears in the above-identified patent and that said Letters Patent is hereby corrected as shown below:

On the Title page, item (60), under "Related U.S. Application Data", in column 1, line 1, delete "60/033,705," and insert -- 61/033,705, --, therefor.

In the Specification

In column 1, line 7, delete "No." and insert -- Nos. --, therefor.

In column 3, line 37, delete "Press." and insert -- Press: --, therefor.

In column 4, line 5, delete "lie." and insert -- like. --, therefor.

In column 5, line 45, delete "akynyl," and insert -- alkynyl, --, therefor.

In column 6, line 28, after "that" insert -- formula --.

In column 6, lines 64-65, delete "unsubstited" and insert -- unsubstituted --, therefor.

In column 8, line 56, delete "$N_{0-20}$" and insert -- $N_{0-2}$ --, therefor.

In column 9, line 4, delete "-heteraryl," and insert -- -heteroaryl, --, therefor.

In column 13, lines 31-35, below "$OCH_3$."
delete "In another embodiment, A is thienyl, furyl, pyridinyl, oxazolyl, thiazolyl, or imidazolyl having 1 or 2 substituents, said substituents being selected from F, Cl, Br, I, $CF_3$, $CH_3$, ethyl, isopropyl, OH, and $OCH_3$.".

In column 23, line 15, delete "(4.4 mL)" and insert -- (4.3 mL) --, therefor.

In column 23, line 25, delete "$CH_2Cl$)" and insert -- $CH_2Cl_2$ --, therefor.

In column 24, line 13, delete "HF pyr" and insert -- HF•pyr --, therefor.

In column 27, line 34, delete "□mol)" and insert -- mmol) --, therefor.

In column 29, line 33, delete "□L," and insert -- mL, --, therefor.

In column 33, line 4, delete "Seperately," and insert -- Separately, --, therefor.

In column 35, line 25, delete "0.01" and insert -- 0.011 --, therefor.

Signed and Sealed this
Twenty-sixth Day of November, 2013

Margaret A. Focarino
*Commissioner for Patents of the United States Patent and Trademark Office*

CERTIFICATE OF CORRECTION (continued)
U.S. Pat. No. 8,487,091 B2

In column 36, line 21, delete "withh" and insert -- with --, therefor.

In column 41, line 57, delete "n," and insert -- rt, --, therefor.

In column 43, line 4, delete "Seperately," and insert -- Separately, --, therefor.

In column 43, line 9, delete "1 lmg" and insert -- 11 mg --, therefor.

In the Claims

In column 44, line 45, in claim 1, delete "cis—$CH_2$—CH—CH—," and insert -- cis—$CH_2$—CH=CH—, --, therefor.